(12) United States Patent
Whitfield

(10) Patent No.: US 9,883,837 B2
(45) Date of Patent: Feb. 6, 2018

(54) HEART RATE AND PULSE MONITORING DEVICE

(71) Applicant: Jonathan M. Whitfield, Dallas, TX (US)

(72) Inventor: Jonathan M. Whitfield, Dallas, TX (US)

( * ) Notice: Subject to any disclaimer, the term of this patent is extended or adjusted under 35 U.S.C. 154(b) by 666 days.

(21) Appl. No.: 14/348,258

(22) PCT Filed: Oct. 1, 2012

(86) PCT No.: PCT/US2012/058261
§ 371 (c)(1),
(2) Date: Mar. 28, 2014

(87) PCT Pub. No.: WO2013/049798
PCT Pub. Date: Apr. 4, 2013

(65) Prior Publication Data
US 2014/0235980 A1    Aug. 21, 2014

Related U.S. Application Data

(60) Provisional application No. 61/541,602, filed on Sep. 30, 2011.

(51) Int. Cl.
*A61B 5/02* (2006.01)
*A61B 5/00* (2006.01)
(Continued)

(52) U.S. Cl.
CPC ............ *A61B 5/7221* (2013.01); *A61B 5/024* (2013.01); *A61B 5/0205* (2013.01);
(Continued)

(58) Field of Classification Search
CPC ....... A61B 5/00; A61B 5/0205; A61B 5/1455; A61B 7/04; A61B 5/024; A61B 5/14551;
(Continued)

(56) References Cited

U.S. PATENT DOCUMENTS

| | | | |
|---|---|---|---|
| 6,178,343 B1* | 1/2001 | Bindszus | A61B 5/0245 600/323 |
| 2004/0249298 A1* | 12/2004 | Selevan | A61B 5/024 600/528 |

(Continued)

FOREIGN PATENT DOCUMENTS

| | | |
|---|---|---|
| JP | 2006518631 | 8/2006 |
| JP | 2008535555 | 9/2008 |
| JP | 2010084286 | 4/2010 |

OTHER PUBLICATIONS

Kamlin et al., "Accuracy of Pulse Oximetry Measurement of Heart Rate of Newborn Infants in the Delivery Room," The Journal of Pediatrics, vol. 152, Issue 6, Jun. 2008, pp. 756-760.*

*Primary Examiner* — Navin Natnithithadha
*Assistant Examiner* — Eric Messersmith
(74) *Attorney, Agent, or Firm* — DeLio, Peterson & Curcio, LLC; Kelly M. Nowak

(57) ABSTRACT

Methods, devices and systems for obtaining heart rate by obtaining apical and non-apical heart rate datum using first and second heart rate monitoring devices. The apical and non-apical heart rate data are input into a heart rate verification module (HRVM) that includes a number of programming instructions for effecting the invention. An apical heart rate measure and non-apical heart rate measure are calculated in the HRVM, and an acceptable heart rate range is generated using the apical heart rate measure. Whether the non-apical heart rate measure is a reliable measure of a true heart rate is identified by determining whether the non-apical heart rate measure falls within or outside the acceptable heart rate range. A split display screen of the HRVM displays the apical heart rate measure, non-apical heart rate measure, and information identifying whether the non-apical heart rate measure falls within or outside the acceptable heart rate range.

20 Claims, 16 Drawing Sheets

(51) Int. Cl.
  *A61B 5/024*   (2006.01)
  *A61B 5/0205*  (2006.01)
  *A61B 7/04*    (2006.01)
  A61B 5/0245   (2006.01)
  A61B 5/1455   (2006.01)
  A61B 7/02     (2006.01)
(52) U.S. Cl.
  CPC ........ *A61B 5/14551* (2013.01); *A61B 5/7278* (2013.01); *A61B 7/04* (2013.01); A61B 5/0245 (2013.01); A61B 5/02416 (2013.01); A61B 5/1455 (2013.01); A61B 7/02 (2013.01); A61B 2503/045 (2013.01)
(58) Field of Classification Search
  CPC ....... A61B 5/7221; A61B 5/7278; A61B 7/02; A61B 5/02416; A61B 5/0245; A61B 2503/045
  See application file for complete search history.

(56) References Cited

U.S. PATENT DOCUMENTS

| | | | |
|---|---|---|---|
| 2006/0058609 A1 | 3/2006 | Olstad | |
| 2008/0154098 A1* | 6/2008 | Morris | A61B 5/02416 600/300 |
| 2012/0232416 A1* | 9/2012 | Gilham | A61B 5/7246 600/515 |

* cited by examiner

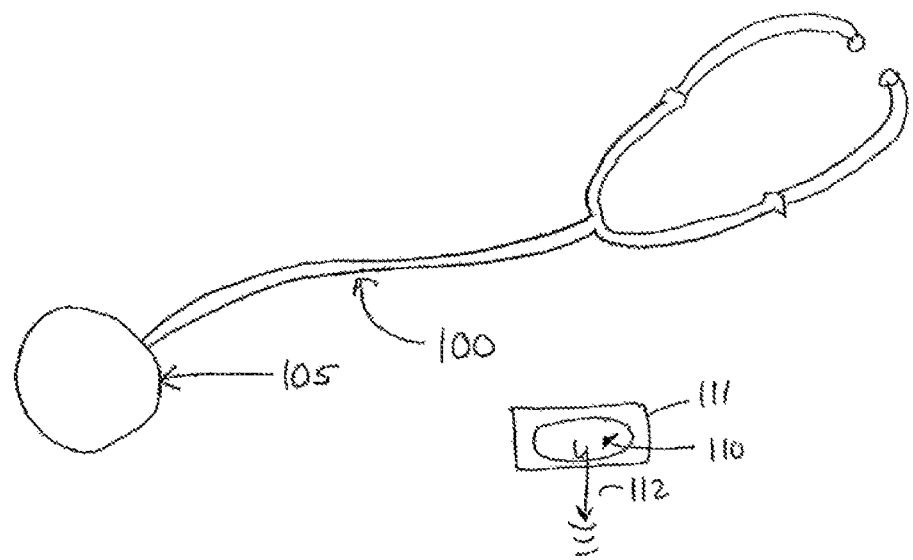
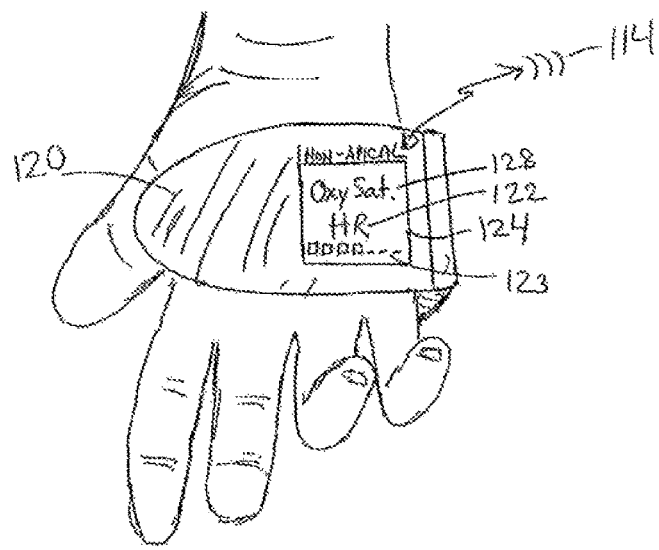
Figure 6
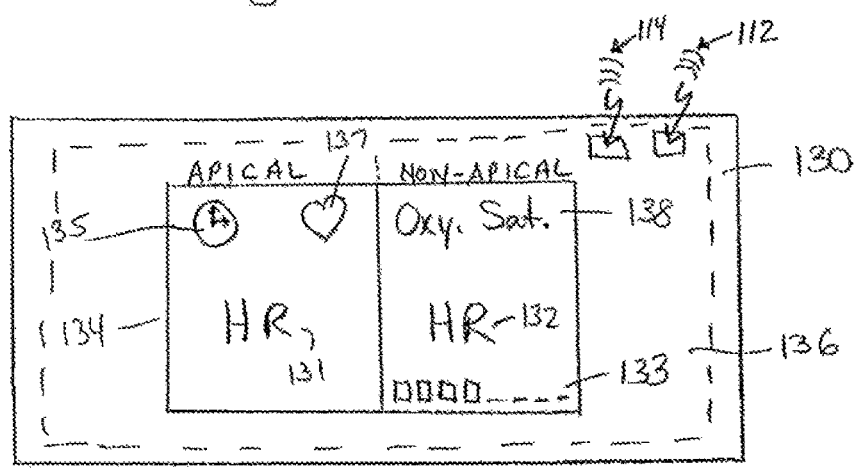

HEART RATE AND PULSE MONITORING DEVICE

PRIORITY

This application claims priority to PCT Application No. PCT/US2012/058261, filed Oct. 1, 2012, which claims priority to U.S. Provisional Application No. 61/541,602, filed Sep. 30, 2011.

BACKGROUND OF THE INVENTION

1. Field of the Invention

The present invention relates in general to the field of heart monitoring, and more particularly, to devices, methods and systems for determining and outputting in real-time the heart rate, pulse and oxygenation of a patient.

2. Description of Related Art

Pulse and heart rate are both well-known measures to obtain vital statistics of a patient. The pulse can be obtained and pulse rate measured at any location on the body where an artery's pulsation can be transmitted to the surface, typically through pressure. For instance, the pulse may be detected, and pulse rate measured, at locations on the body where an artery can be pressed against bone, including, at the neck (carotid pulse), wrist (radial pulse), finger, hand, foot, etc. At any of these locations, the pulse may be measured by a medical professional pressing their fingers down on the location to feel the pulse and count the number of pulses or beats at such location.

The pulse and pulse rate may also be detected and measured through indirect methods. One such indirect approach is through the measure of light absorption of varying wavelengths in a patient's blood to determine the oxygenation of the patient's hemoglobin. This technique is known as pulse oximetry. Conventional pulse oximetry uses a sensor placed on a thin part of the patient's body, whereby light at red (660 nm) and infrared (940 nm) wavelengths is passed sequentially through the patient to a photodetector. Oxygenation of the blood is measured based upon the ratio of changing absorbance of such red and infrared light through spectral anaylsis. Once measured, both the obtained oxygen level and pulse rate are then displayed on a monitor to the medical professional(s).

Pulse oximetry data is important whenever a patient's oxygenation may be unstable, such as, for instance in intensive care, surgery, emergency and even at birth. However, current pulse oximeters used to detect and measure pulse and pulse rate have a lag time. This lag time extends from the time the pulse oximeter is applied to the patient, to the time a pulse is detected, to the time needed to calculate oxygen level and pulse rate, to the final output of such measures to the medical professional. When time is of the essence, especially at birth when mere seconds are critical to the well-being of the newborn, any such lag time is undesirable. Known pulse oximeters are also influenced by several external conditions including, altitude, temperature, lighting, involuntary movements and nail polish, that affect the accuracy and validity of the readings output by such conventional pulse oximeters. Internal conditions of the patient may also affect the output readings of known pulse oximeters.

Heart rate is another vital statistic, and is often used interchangeably with pulse rate. Heart rate is the number of heartbeats per unit of time, often expressed as beats per minute (i.e., bpm). The heart rate measure may be the same as, or different from, the pulse rate measure.

One approach of obtaining heart rate is by finding a pulse on the patient, counting the pulses or beats, and then calculating the heart rate. For instance, the radial pulse resides at the wrist whereby the radial pulse is felt and measured to obtain a radial pulse rate. Alternatively, the pulse may be detected auditorily and listened-to-beats counted. For an essentially accurate reading, heart rate is obtained by measuring the pulse at a point of maximal impulse (PMI). This type of pulse is referred to as an apical pulse and is generally taken with a stethoscope located on the left side of the chest, about 2 inches to the left from the end of the sternum. As such, an apical heart rate is obtained by taking the pulse over the apex of the heart. An apical heart rate is generally a more accurate and reliable measure of heart rate, as compared to obtaining a heart rate at a location other than at the apex of the heart (e.g., as compared to obtaining a radial pulse/heart rate at the radial bone of the wrist).

In most cases, the apical heart rate will equal heart rates obtained at other locations across the body (i.e., at non-apical pulse locations), and vice versa. However, when the apical heart rate is higher than the non-apical heart rate (e.g. the radial pulse/heart rate), a pulse deficit is observed. This pulse deficit indicates that there is a problem with the blood getting to the arterial point at which such non-apical pulse was taken. Medical attention is often required in such situations. While a pulse deficit may be observed with the apical pulse being lower than the radial pulse, such an occurrence is typically due to human and/or mechanical error.

The heart rate may also be measured using a heart-monitoring device that has a probe positioned over the patient's heart for outputting a heart rate measure to a medical professional. This enables the medical professional to both diagnose and monitor various medical conditions.

One example of a heart-monitoring device is taught in U.S. Pat. No. 6,210,344, issued to Perin, et al., for a method and apparatus for passive heart rate detection. Briefly, this reference teaches a method and apparatus for measuring the heart rate of a patient, which includes a hollow bell mounted on a diaphragm. A transducer element is positioned to receive sound transmitted through the diaphragm, convert the sounds into electrical impulses, and transmit the electrical impulses to a microprocessor. The electrical impulses have real-time wave patterns corresponding to the real-time wave patterns of the original sounds. The microprocessor performs mathematical operations on wave pattern data conveyed by the electrical impulses to determine a numerical value corresponding to the frequency of the wave patterns. This numerical value is sent to a digital output and displayed thereon.

U.S. Pat. No. 5,218,969, issued to Bredesen, et al., discloses an intelligent stethoscope. This intelligent stethoscope is used for performing auscultation and for automatically diagnosing abnormalities based on body sounds wherein the body sounds are received, digitized and stored in memory. The body sounds are recorded from a plurality of locations on the body, and all of the sounds are categorized according to specific characteristics to form a matrix of information. The generated matrix is then compared against a plurality of stored matrices using a technique similar to analysis. Each of the stored matrices contain information indicative of known abnormalities such as specific heart murmurs, lung abnormalities, etc. When a matrix match is found, the diagnosis is displayed on an LCD display formed in the body of the stethoscope. The LCD display is also capable of displaying a visual representation of the recorded body sounds.

Still another prior art reference, U.S. Pat. No. 4,436,096, issued to Dyck, et al., discloses a portable digital heart rate meter/stethoscope. This prior art reference discloses that electrical signals corresponding to heart sounds detected by a pulse/sound transducer are filtered in a narrow band pass filter, whose pass band is centered on a characteristic heart sound frequency of 33 Hz. The filter improves signal-to-noise ratio and enables the transducer to be used over a patient's clothing. The unfiltered signal is amplified and fed to binaural leads to provide the function of an electronic stethoscope. In addition, the filtered signal is converted into pulses in response to which a count corresponding to the detected heart rate is established in a counter and displayed as a digital heart rate indication.

While known mechanical heart rate and pulse monitoring devices are each individually useful after baseline information has been attained, such as those described above, they are not useful when time is of the essence and only a hands-on auscultation is reliable. Furthermore, such known devices do not allow the entire medical team to have a comprehensive awareness of the medical condition of the patient in an immediate and reliable manner. Accordingly, a need continues to exist in the art for improved heart rate and pulse monitoring devices that can be relied on when time is of the essence, and subsequent to such time.

SUMMARY OF THE INVENTION

Bearing in mind the problems and deficiencies of the prior art, in one or more embodiments the invention provides methods of obtaining heart rate that include obtaining apical heart rate data using a first heart rate monitoring device and obtaining non-apical heart rate data using a second heart rate monitoring device. The apical heart rate data and the non-apical heart rate data are both input into a heart rate verification module. An apical heart rate measure and a non-apical heart rate measure are both calculated in the HRVM. An acceptable heart rate range is then generated in the HRVM using the apical heart rate measure. Whether the non-apical heart rate measure is a reliable measure of a true heart rate is identified by determining whether the non-apical heart rate measure falls within or outside the acceptable heart rate range.

In other embodiments the invention is directed to devices for obtaining heart rate that include a heart rate verification module that receives apical heart rate data from a first heart rate monitoring device and non-apical heart rate data from a second heart rate monitoring device. The heart rate verification module may include a first set of instructions that calculate apical and non-apical heart rate measures, and a second set of instructions that generate an acceptable heart rate range using the apical heart rate measure. The heart rate verification module may also include a third set of instructions that determines whether the non-apical heart rate measure falls within or outside the acceptable heart rate range. A display screen of the heart rate verification module displays the apical heart rate measure, non-apical heart rate measure, and information identifying whether the non-apical heart rate measure falls within or outside the acceptable heart rate range.

Still other embodiments of the invention are directed to systems for obtaining heart rate that include first and second heart rate monitoring devices for respectively obtaining apical heart rate data and non-apical heart rate data. The system also includes a heart rate verification module that receives the apical heart rate data and non-apical heart rate data. The heart rate verification module may include a first set of instructions that calculate apical and non-apical heart rate measures, and a second set of instructions that generate an acceptable heart rate range using the apical heart rate measure. The heart rate verification module may also include a third set of instructions that determines whether the non-apical heart rate measure falls within or outside the acceptable heart rate range. A display screen of the heart rate verification module displays the apical heart rate measure, non-apical heart rate measure, and information identifying whether the non-apical heart rate measure falls within or outside the acceptable heart rate range.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

FIG. 6 illustrates still other components of one or more embodiments of the present invention.

DESCRIPTION OF THE PREFERRED EMBODIMENT(S)

In describing the preferred embodiment of the present invention, reference will be made herein to FIGS. 12A-D of the drawings in which like numerals refer to like features of the invention.

While the making and using of various embodiments of the present invention are discussed in detail herein, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

Virginia Apgar described the scoring system now used worldwide to evaluate newborns in the first minutes of life as being five (5) factors, and scored each item from 0 to 2. These five (5) factors include color, cry, grimace, tone and heart rate, each being weighted equally. With the passage of time it became apparent that heart rate was the key element in evaluating the newborn in the first minutes of life. Heart rate is a key marker for cardiac output, which is primarily rate-driven in the newborn and young infant.

While the present invention is suitable for use with any patient in need of heart rate and/or pulse monitoring and/or detection, it is particularly beneficial for obtaining heart rate and pulse in situations where time is of the essence. One such instance is in the use for obtaining accurate and reliable heart rate and pulse measures in a newborn within the first few seconds to minutes after birth. While particular reference is made herein to obtaining heart rate in a newborn, it should be appreciated and understood that the invention is suitable for use with any patient, at any age, whether human or non-human.

Figure 1:
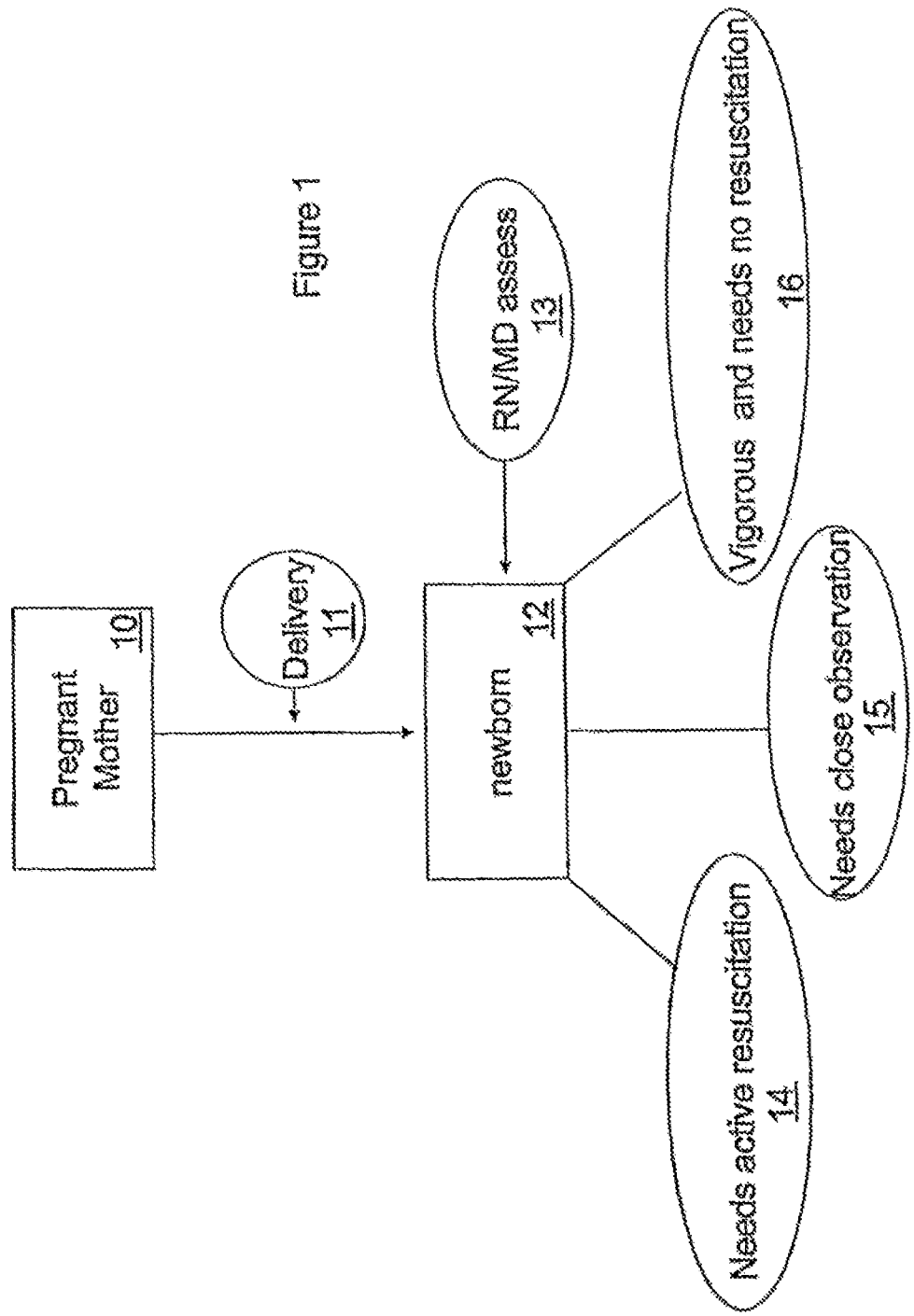
FIG. 1 is a flowchart summarizing the decision making for treatment of a newborn upon birth.

Monitoring of a newborn's heart rate is essential and guides the established decision making algorithms for newborn resuscitation. Heart rate measures guide the medical professional's decision making processes in following such algorithms for the next steps of neonatal resuscitation. FIG. 1 illustrates a flowchart summarizing one such algorithm for the decision making process for treatment of a newborn upon birth. When a pregnant mother 10 approaches the time for delivery 11, the medical team will prepare for the arrival of the newborn 12. The registered nurse and/or medical doctor 13 assess the condition of the newborn 12 and make a determination whether the newborn needs active resuscitation 14, close observation 15, or is vigorous and as such needs no resuscitation 16.

Resuscitation of the newborn is primarily driven by the newborn's caretakers assessing the newborn in the delivery room. These caretakers may include doctors, nurses and other medical professionals and/or support staff. One such assessment routinely carried out by the newborn's caretakers, at nearly all deliveries, is precordial auscultation of the newborn's heartbeat and determination of the heart rate (i.e., heart exam by listening to the heart). An increasing heart rate into the normal range in the first minutes of life is evidence of a normal transition to extra-uterine life.

In normal practice of precordial auscultation, the heart rate is estimated by a medical caretaker simultaneously auscultating (i.e., listening to) the precordium of the newly born infant and counting the detected (i.e., heard) heart beat over a 6 second time period, typically using the second hand of a watch or clock. The caretaker multiplies this number by a factor of 10 to obtain the estimated heart rate, which is measured in beats per minute (BPM). Most often, precordial auscultation is accomplished by the caretaker listening to the newborn's heart rate manually through a stethoscope and using a wristwatch counting the number of heard beats over certain amount of time, e.g., 6 seconds or even 10-20 seconds. After this time period, the caretaker mentally arrives at a possible calculation of a heart rate.

Figure 2:
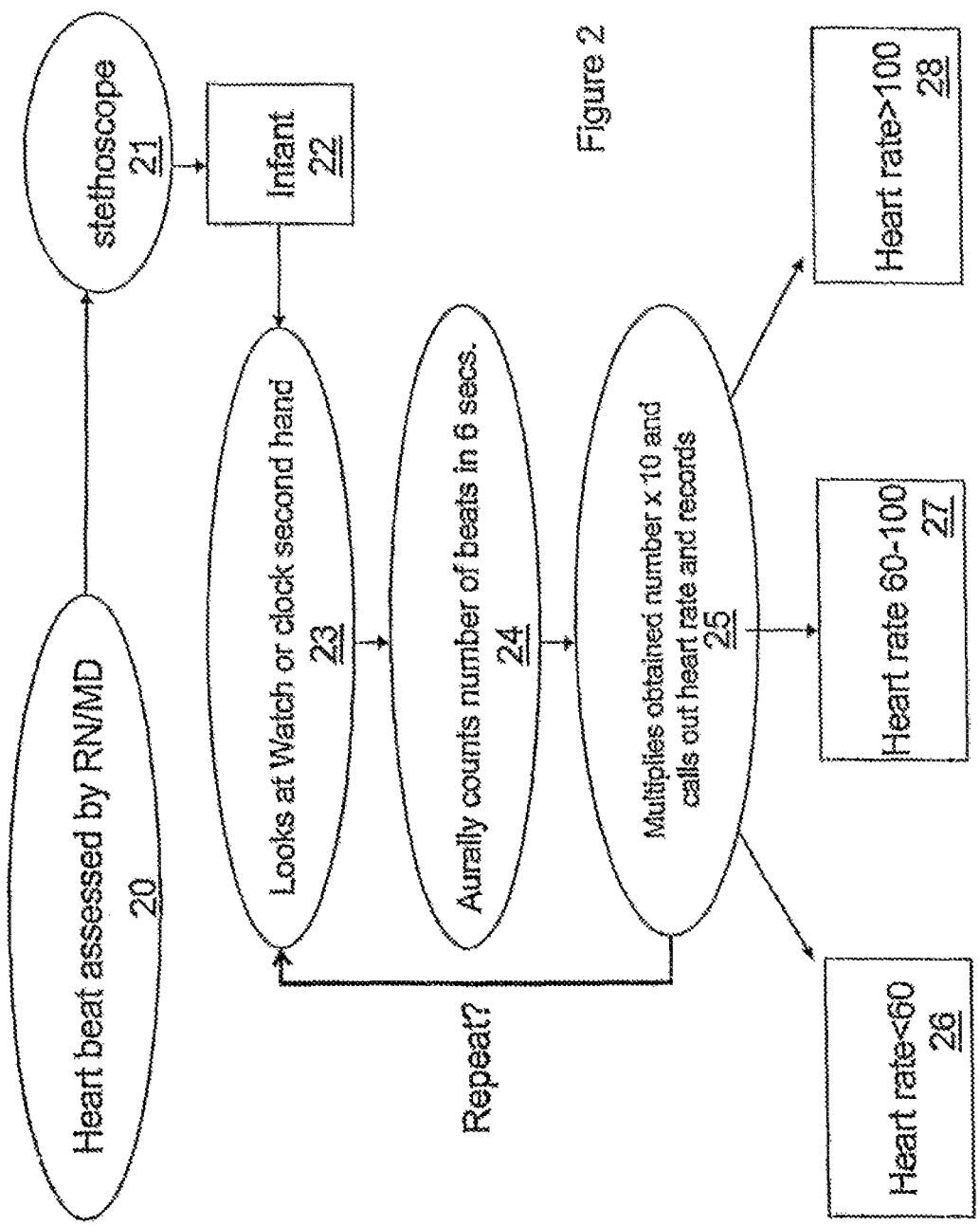
FIG. 2 is a flowchart summarizing the decision making for the on-going evaluation of a newborn upon the determination that the patient may be under distress.

For instance, referring to FIG. 2, the heartbeat is assessed by an RN or MD (step 20) using a stethoscope 21 on the infant 22, while the RN/MD looks at a clock or a watch 23, and counts the second hand 24. In step 24, the RN or MD counts the number of aurally detected heartbeats in approximately 6 seconds, and then mentally calculates the heartbeat by multiplying the number of heartbeats counted in the approximately 6 seconds by a factor of 10. The calculated heartbeat may, or may not, be recorded 25. This heart rate number is communicated, typically yelled out, to the other team members responsible for resuscitation. During the intense atmosphere of a newborn resuscitation, these activities are often challenging, even to those individuals or medical caretakers experienced at such practices. When inexperienced individuals and caretakers are responsible for resuscitation the problems are magnified. Additionally, these manually obtained and calculated heart rates are at best an estimate, and are rarely accurate.

Figure 3:
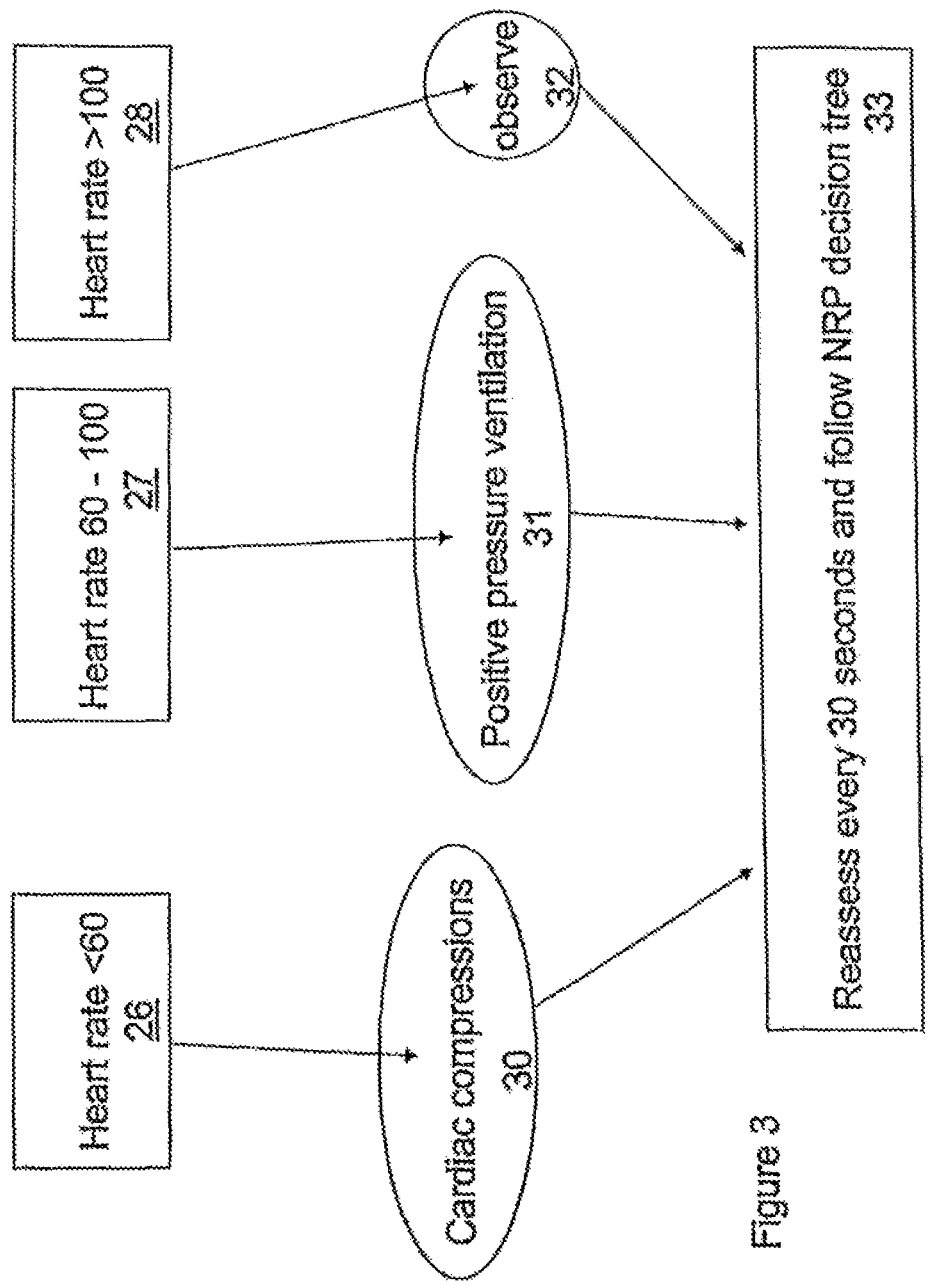
FIG. 3 is a flowchart summarizing the decision making for the treatment of a newborn upon a determination that the patient may be under distress.

Based on the initial heart rate determination, or one or more subsequent determinations, the RN/MD determines if the infant has a heart rate of less than 60 (26), between 60 and 100 (27), or greater than 100 (28) heartbeats per minute. The normal heart rate in the newborn is 120 to 160 heartbeats per minute. Referring to FIG. 3, depending on whether the infant had a heart rate of less than 60 (26), between 60 and 100 (27), or greater than 100 (28) heartbeats per minute, the medical team may, respectively, initiate cardiac compressions 30, provide positive pressure ventilation 31, or continue to observe 32 the infant.

In particular, the newborn with a heart rate over 100 heartbeats per minute and with the rate rising requires minimal assistance. However, an infant with a heart rate less than 100 heartbeats per minute requires ventilation assistance. Those with heart rates less than 60 heartbeats per minute, and are not responding to ventilation after 30 seconds, require external cardiac massage to support cardiac output. The condition of the infant is reassessed (step 33) every 30 seconds and the Neonatal Resuscitation Protocol (NRP) is subsequently followed. In the prior art, each of these steps is manually conducted by one or more caretakers of the medical team tending to the newborn, and are based on ad hoc timing depending on the circumstances surrounding the infant and without any indicator of timing.

Acquisition of the skills required for performing precordial auscultation to quickly and accurately assess, and then communicate, heart rate to the resuscitation team are challenging and inefficient. These challenges are increased as tense developments arise in the delivery room, often during emergency newborn resuscitation situations. Simulation studies have shown that when tensions are increased during these critical resuscitation events, the auscultation and calculation of estimated heart rate by medical caretakers is often incorrect, for instance, it may be incorrect up to about 52% of the time. This ultimately leads to errors in medical interventions, whether they are unnecessary/inappropriate medical interventions or steps taken or unacted upon medical interventions or steps not taken. For example, overestimation of a heart rate that is in reality <60 beats per minute may result in a delay in chest compressions.

Aside from precordial auscultation, the heart rate may be obtained by palpation of other pulses including, for example, palpation of the newly cut umbilical, as well as through the application of sensors. However, precordial auscultation remains to be the most reliable clinical technique for measuring heart rate in the newly born infant during and throughout the first minutes of life. Umbilical cord pulsation tends to be an unreliable measure of heart rate, since it may often be less than 100 beats per minute or even undetectable or absent.

As for electronic monitors, application of conventional electrodes for EKG or a sensor for a pulse oximeter take time and must be verified manually before a determination is made that the electronic devices are connected properly and that their operation is accurately reflecting the newborn's true heart rate. This may take at least 1 to 2 minutes, if not more, before such electronic monitors are attached in the delivery room after the birth of an infant requiring resuscitation. Also, after the attachment time has lapsed, it may take an additional 1 to 2 minutes, or more, (hence a total of 2 to 4 minutes, or more, in all) before reliable readings are obtained and observed by the newborn's caretaker.

Another disadvantage of some conventional electronic monitors is that only certain medical professional may have immediate heart rate information, which is often delivered in a high tension, high stakes environment by speaking or verbally announcing the manually obtained estimate of heart rate to other medical team members at a specific time, or time intervals. Also, even after leads for EKG or pulse oximeters are applied and a signal obtained, the validity of the heart rate must be double checked by auscultation with a stethoscope. In situations where cardiac output is low and heart rate is low, the independently operated electronic devices for monitoring heart rate are often problematic, time consuming, and repeated manual auscultation is required.

In one or more embodiments, the present invention provides apparatus, systems and methods that efficiently, quickly and reliably assess a newborn within the first few seconds of delivery, and the 90 seconds thereafter, by providing a reliable heart rate measure output to substantially the entire medical team, and which is verified as being an accurate reading of the newborn's true heart rate within such time frame.

Figure 4A:
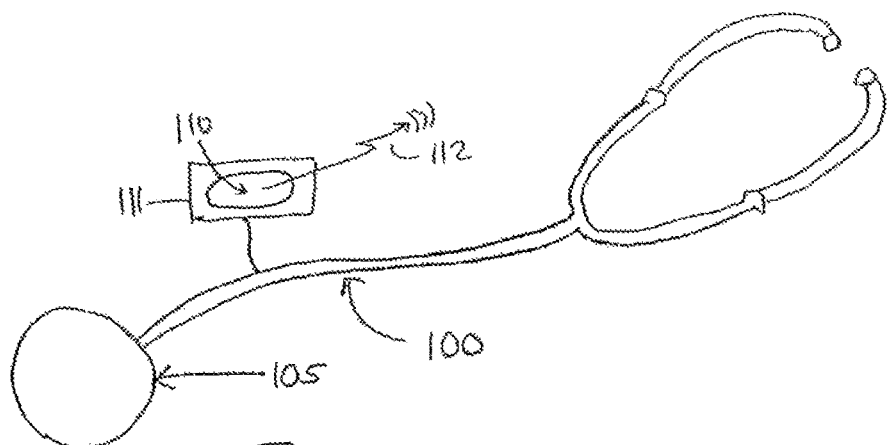
FIGS. 4A-C illustrate various components of one or more embodiments of the present invention.
Figure 4B:
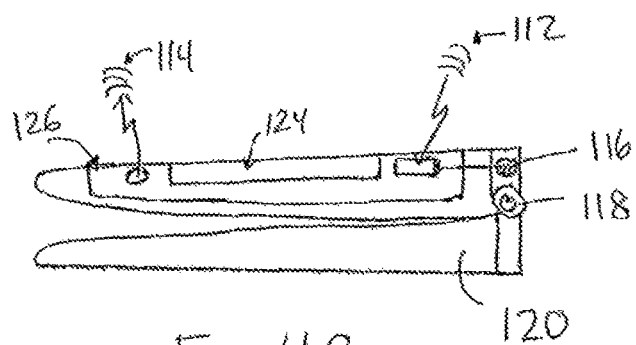
Figure 4C:
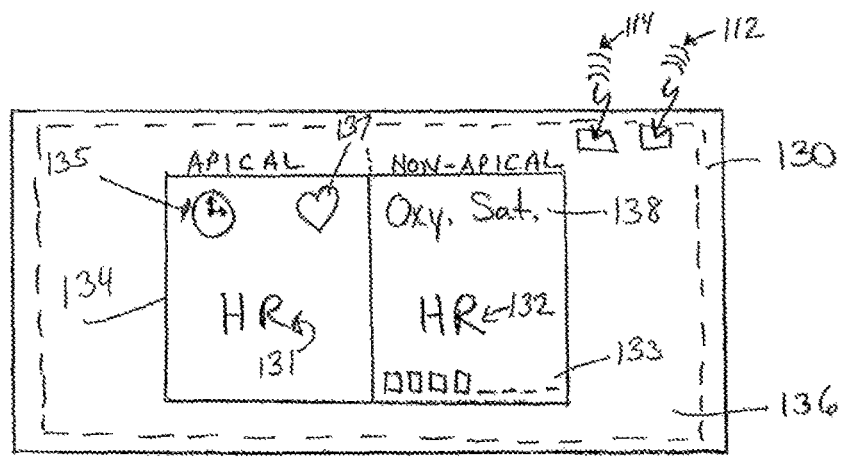

Referring to FIGS. 4A-C, components of various embodiments of the invention are known, including, a first heart rate monitoring device 100, a second heart rate monitoring device 120, a Heart Rate Verification Module 126, 136, and optionally a display device 130. In one or more embodiments, the first heart rate monitoring device 100 may include a heart rate instrument having a probe 105 for attaining an auscultated heart rate. While not meant to limit the invention, in various embodiments the first heart rate monitoring device 100 may be a stethoscope 100 having a probe 105 for listening to a patient's pulse to attain a heart rate in accordance with the invention. More preferably, the stethoscope is placed over the apex of the patient's heart to obtain an apical heart rate reading. In one or more embodiments the stethoscope may be a stethoscope as described in PCT Patent Application No. PCT/US2011/036029, which is incorporated by reference herein.

As shown in FIG. 4A, the first heart rate monitoring device 100 also includes an actuating component 111 capable of being actuated by the user listening to the newborn's (or patient's) heart beat. This actuating component may include an actuator 110 that may be pressed or activated every time the user hears a heart beat. The actuator 110 may be, for example, a button, knob, key, etc. In one or more embodiments, the actuating component 111 may be a force detector having an actuator pressed by an operator. It should also be appreciated that while the actuating component 111 is shown attached to the heart rate monitoring device 100 in FIG. 4A, this actuating component 111 may be a component separate from the first heart rate monitoring device 100 as shown in FIG. 6. As such, a user may hold the first heart rate monitoring device 100 in one hand at a predetermined location on the patient, while in the other hand the user holds the actuating component 111 and activates the actuator 110 (i.e., button, knob, key, etc.) every time the user hears a heart beat via the first heart rate monitoring device 100.

Figure 5:
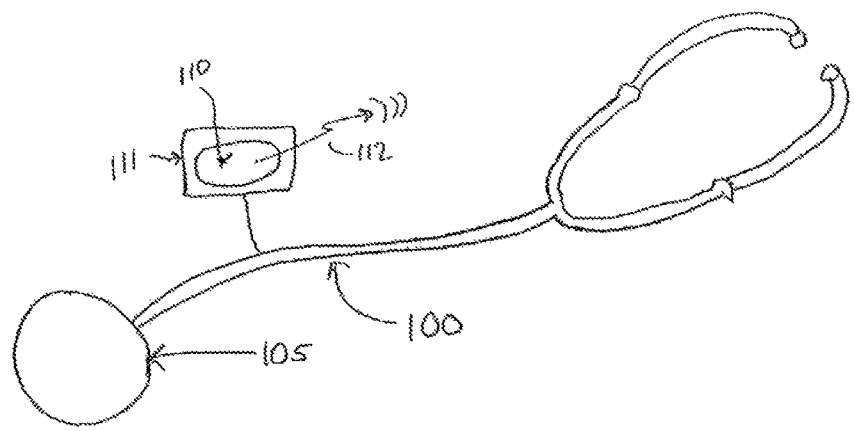
FIG. 5 illustrates alternate components of one or more embodiments of the present invention.
Figure 5:
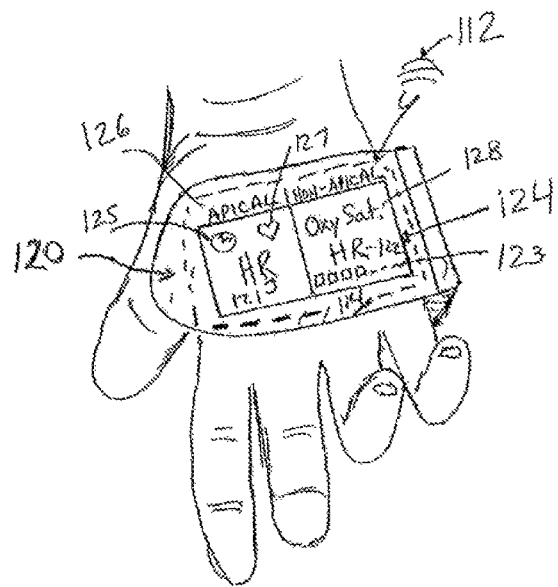

Upon pressing or activating the actuator 110 a signal is generated in the actuating component 111. This signal is transformed into an electrical signal 112 that is transmitted out from the actuating component 111. The signal 112 may be a wireless signal, or alternatively, it may be transmitted via wiring. The electrical signal 112 is received by a receiver of a Heart Rate Verification Module (hereinafter "HRVM") 126, 136. In one or more embodiments, the HRVM 126 may reside within the second heart rate monitoring device 120 (as shown in FIGS. 4B and 5). In alternate embodiments, the HRVM 136 may reside within a display device 130 that is separate from both the first 100 and second 120 heart rate monitoring devices (as shown in FIGS. 4C and 6).

In accordance with the various embodiments of the invention, the second heart rate monitoring device 120 may be an instrument that is attached to, or in communication with, a location that is remote from the predetermined location at which the first heart rate monitoring device 100 is positioned on the patient. In this manner the heart rate can be obtained at two different locations on the patient. As shown in FIGS. 4B and 5, in one or more embodiments, the second heart rate monitoring device 120 may be a pulse oximeter attached to the patient at locations where a pulse reading can be obtained including, but not limited to, a hand, foot, finger, and the like. In one or more preferred embodiments, wherein the invention is implemented on a newborn in the first few seconds to minutes after birth, the first heart rate monitoring device 100 may comprise a stethoscope while the second heart rate monitoring device 120 may comprise a pulse oximeter that is attached to either the newborn's hand or foot.

Referring to FIGS. 4B and 5, in those embodiments where the second heart rate monitoring device is a pulse oximeter, the pulse oximeter may include a spring 118 for opening, closing, clipping and securing the pulse oximeter onto the patient. It may also include a battery 116 that is connected to the HRVM 126 of the invention. The battery 116 may be rechargeable, or it may be a disposable and replaceable battery. The pulse oximeter detects a non-apical heart rate of the patient as well as the patient's blood oxygenation saturation.

The second heart rate monitoring device 120 (e.g., the pulse oximeter) generates a signal 114 that corresponds to a measured non-apical heart rate. This signal 114 is transmitted from the second heart rate monitoring device to the HRVM 126, 136. Again, the HRVM 136 may reside within a display device 130 separate from both the first and second heart rate monitoring devices (see, e.g., FIGS. 4C and 6), or the HRVM 126 may reside within the second (or even the first) of the heart rate monitoring devices (i.e., within the pulse oximeter) (see, e.g., FIGS. 4B and 5). Regardless of whether the HRVM resides within one of the heart rate monitor devices, or in the separate display device 130, the HRVM receives signals 112, 114 from both the actuating component 111 and the second heart rate monitoring device 120, respectively, for analysis and interpretation thereof.

Figure 7A:
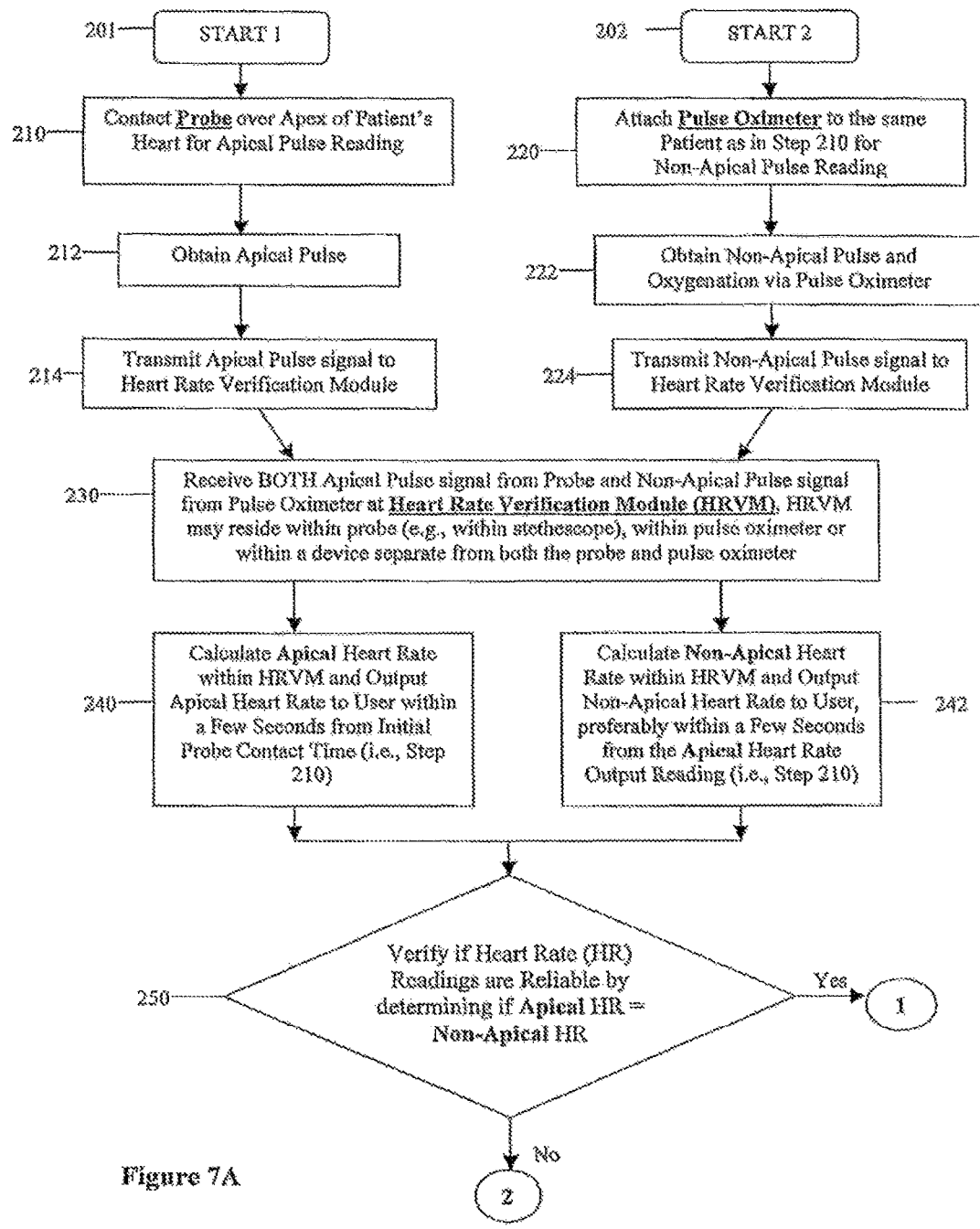
FIGS. 7A-C illustrate a flowchart in accordance with one or more embodiments of the present invention.
Figure 7B:
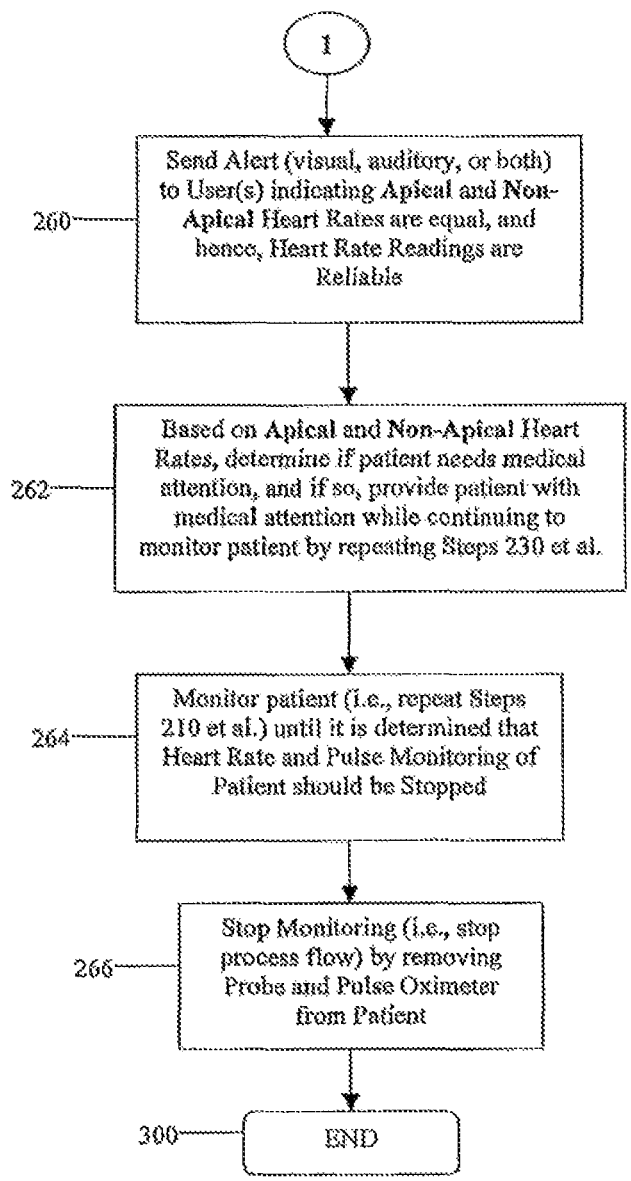
Figure 7C:
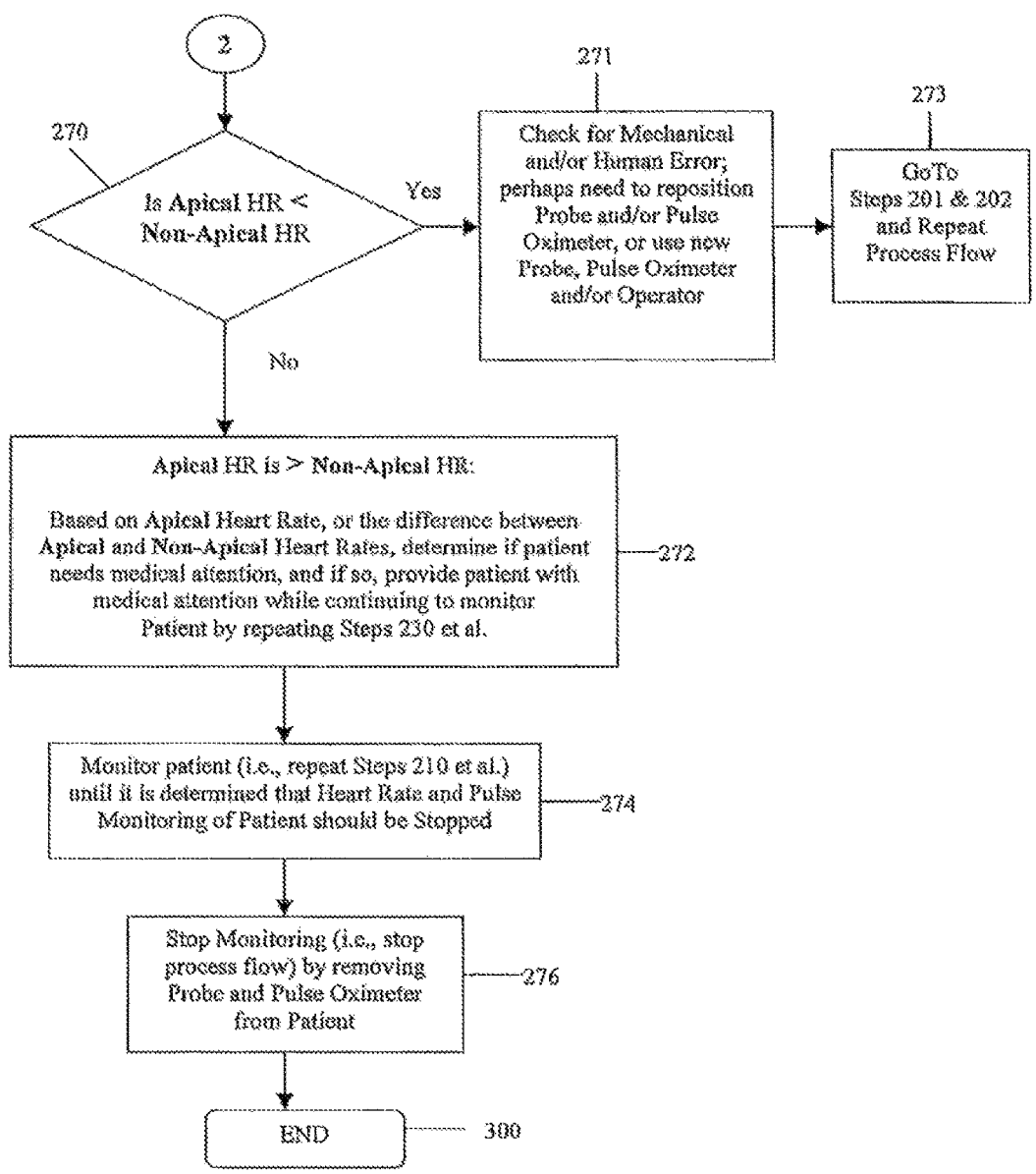

For ease of understanding the invention, reference is made to the process flow shown in FIGS. 7A-C, however, it should be appreciated and understood in accordance with the foregoing description of the invention that other process flows may be implemented for carrying out the present invention. Reference is also made to FIGS. 4A-6.

The process is started by a medical caretaker/personnel positioning the probe 105 of the first heart rate monitoring device 100 over the apex of the patient's heart (step 201). The caretaker obtains the apical pulse by listening for such apical pulse and activating the actuator 110 of the actuating component 111 every time a pulse or heartbeat is heard (step 210). This actuation is generated into a signal 112 that is transmitted from the actuating component 111 to the Heart Rate Verification Module 126, 136 (step 214).

As is shown, in (step 230) the HRVM 126, 136 receives the output signal 112 of auscullated heart beats from the actuating component 111. The signal 112 may be transmitted and received for every instance of activation of the actuating component 111 (i.e., after each time a heart beat is heard and the button on the actuating component pressed). Alternatively, the signal 112 may be sent at predetermined set intervals, such as, every 3-10 seconds. In one or more preferred embodiments, the first heart rate monitoring device is positioned over the apex of the heart so that the obtained signal 112 from such readings correlates with the apical heart rate. The HRVM 126, 136 receives this data and electronically calculates, either in real-time or at set intervals (e.g., every 3 seconds, every 6 seconds, etc.), the apical heart rate (step 240). As such, the need for human counting and calculation of the heart rate at set intervals, and as such, human error, is avoided. The user simply needs to activate, press, click, etc. the actuator 110 every time a heart beat is heard via the first heart rate monitoring device.

The HRVM 126, 136 includes, or is in communication with, a display screen 124 or 134 that resides either within the second heart rate monitoring device 120 or the independent display device 130, respectively. The display screens 124, 134 may be split screens that show apical heart rate data on one side and non-apical heart rate data on the other side. For instance, the apical side of the display screen 124, 134 may include apical heart rate 121, 131, along with a timer 125, 135. The timer may be activated at the beginning of a heart rate monitoring session, or at a time when the first and/or second heart rate monitors are applied to the patient. In those embodiments where the present invention is initiated at the critical time of birth, the timer may be activated as soon as the newborn is birthed so that timing and monitoring may begin as quickly as possible (i.e., within the first few (3) seconds of life). The timer 125, 135 may display lapsed time in minutes and seconds.

The apical side of the display screen 124, 134 may also include a confirming unique indicator 127, 137 that may have both a unique shape and be color-coded. For instance, while not meant to be limiting, in the drawings the unique indicator 127, 137 is shown as a heart shape. In one or more embodiments, the unique indicator confirms receipt of the signal 112 from the first heart rate monitoring device 100. In confirming receipt of the transmitted signal 112, the unique indicator 127, 137 may output an identifier or signal (e.g., it may flash) to confirm that the signal 112 from the actuator component 111 is actually being received at the HRVM. In doing so, each time the actuator 110 is activated, pressed, clicked, etc., the unique indicator 127, 137 may flash or blink in sync with each activation to confirm that the HRVM is in fact receiving the transmitted signal 112.

Referring to the non-apical heart rate measure side of the display screens 124, 134 (the process flow of which is discussed in more detail below), this side of the split display screens includes a calculated blood oxygenation saturation reading 128, 138 and an electronically calculated non-apical heart rate 122, 132. The non-apical heart rate is calculated by the HRVM using the received input signal 114 from the second heart rate monitoring device 120 (e.g., from the pulse oximeter). The non-apical side of the display screen also includes a unique identifier 123, 133 for confirming receipt of respective signal 114 from the second heart rate monitoring device. This unique identifier 123, 133 may also indicate the strength of the received signal 114. For instance, the non-apical signal identifier may be a pulsating sensor bar that indicates strength of signal 114 received from the second heart rate monitoring device 120. In observing the signal strength, the fewer number of bars shown on the screen, the lower the strength of the received signal 114, and vice versa for a stronger signal 113. This strength of the signal 114 also correlates with the strength of the pulse obtained at the location of the second heart rate monitoring device.

It should be appreciated and understood that the HRVM 126, 136 includes a unique set of instructions (e.g., a unique program) that enables the present invention to determine and output, in real-time, at least two heart rate readings of a patient for alerting caretakers of critical heart rate ranges, and verifying that the non-apical heart rate measure accurately reflects the patient's true heart rate.

Referring again to the exemplary process flow shown in FIG. 7A, once the HRVM 126, 136 receives the apical heart rate signal 112 (step 230), the HRVM begins to automatically calculate and display the apical heart rate 121, 131 (step 240). This apical heart rate may be continuously calculated and displayed in substantially real-time as the signal 112 is received at the HRVM, or it may be repeatedly calculated and displayed at set intervals (e.g., at every 3-10 seconds).

The apical heart rate 121, 131 is preferably uniquely displayed (e.g., color coded) to alert the caretakers to the recommended interventions needed at critical heart rates. For example, a heart rate of 60 or less beats per minute in a newborn may be displayed and color coded in a first color (e.g., red), while 60 to 100 heartbeats per minute may be color coded in a second color (e.g., amber/orange), and still further, heart rates over 100 per minute may be color coded in a third color (e.g., green). Either all or the majority of the medical personnel/team attending to the patient are then immediately informed of the electronically calculated apical heart rate within about 3-10 seconds from precordial auscultation (i.e., from contact of the probe 105 to the patient), and even within as little as 2 seconds.

Again, the caretaker listening to the apical heart rate activates the actuator 110 each time a heart beat is heard, whereby a signal 112 is generated and transmitted to the HRVM. That is, counting of the number of beats and calculation of the apical heart rate by the caretaker is avoided. Data indicating a state or measure of the apical heart rate may be visually displayed or auditorily announced to the medical personnel. For instance, apical heart rate 121, 131 may be visually displayed on the display screen associated with the HRVM, as well as an auditory signal relating to such heart rate 121, 131 being output to the medical personnel/team.

Based on only the apical heart rate output by the HRVM (i.e., before the non-apical monitoring begins), the medical personnel are apprised (either visually or auditorily) of the patient's apical heart rate in an immediate and rapid response time, typically, within 3-10 seconds of initiating the apical heart rate reading. These medical personnel are apprised of the patient's apical heart rate within mere seconds, which is essential when time is of the essence. Again, such time sensitive settings include, but are not limited to, emergency rooms, at delivery or birth, intensive care units (e.g., neonatal intensive care units), first responder responses (e.g., ambulatory responses), and the like.

In accordance with the invention, the precordial auscultation and rapid translation of the signal associated therewith within mere seconds into a visual and/or auditory alert transmitted to medical personnel avoids the undesired lag time inured by the use of conventional electronic devices. Again, conventional electronic devices often take anywhere from 2 to 4 minutes, or more, before a reliable reading is obtained since it often takes at least 1 to 2 minutes to position the device on the patient, and another at least 1 to 2 minutes to detect the heart beat and obtain a heart rate. Sometimes the step of generating the heart rate takes an additional 1 to 2 minutes beyond the step of detecting the heart beat, thereby increasing the total lag time of conventional electronic devices to range from about 3 to about 6 minutes, or more. This lag time is avoided in accordance with the various embodiments of the invention, which provides a fast, reliable measure of apical heart rate that is output to a majority of the medical personnel/team attending to the patient.

With the HRVM 126, 136 providing substantially the entire medical personnel with an apical heart rate in mere seconds, any medical treatment needed in response to such output apical heart rate may be quickly administered by the entire medical team thereby increasing success of response to such treatment. For instance, when the apical heart rate 121, 131 is displayed using color-coded indicators the entire medical team will be apprised of the patient's heart rate status and will be able to act accordingly. As an example, a heart rate displayed in red may indicate to the medical team that the patient's heart rate is 60 BPM, or less, such that the patient requires medical treatment (e.g., initiate cardiac compressions 30), a heart rate displayed in amber/orange may indicate that the patient's heart rate is 60 to 100 BPM and may require different medical treatment (e.g., provide positive pressure ventilation 31), while a heart rate displayed in green may indicate that the patient's heart rate is over 100 BPM and the patient appears to be stable (may continue to observe 32 the patient).

Referring to steps associated with the non-apical heart rate in FIG. 7A, while the apical heart rate is continuously being measured and alerted to the medical personnel, determination of the non-apical heart rate is started (step 202). The second heart rate monitoring device is attached to the patient (steps 202), pulse rate readings obtained (step 220) and transmitted via signal 14 to the HRVM 126, 136 (step 224). Like that of the apical heart rate 121, 131, the HRVM electronically calculates the non-apical heart rate 122, 132 (step 242) and outputs it to the medical team. In the various embodiments of the invention, the non-apical heart rate may or may not be color-coded. Preferably, the non-apical heart rate is output within a few seconds from the output of the apical heart rate output, and most preferably the non-apical and apical heart rates may be output simultaneously.

Once a non-apical heart rate 122, 132 is obtained, the HRVM automatically analyzes and compares the apical heart rate to the non-apical heart rate to determine whether the two heart rate measures are substantially equal (step 250). If the two heart rate measures are substantially equal, then the non-apical heart rate can be trusted as an accurate reading of the patient's true heart rate, and the process flow continues to step 260 (as shown in FIG. 7B). If the apical heart rate and non-apical heart rate are determine to be not substantially equal to one another, then the process flow continues to step 270 (as shown in FIG. 7C).

In one or more preferred embodiments, the determination in step 250 of whether the apical and non-apical heart rates are substantially equal to each other may be accomplished by determining whether the apical heart rate and the non-apical heart rate fall within a predefined acceptable range of deviation. In these embodiments, the acceptable range of deviation is used to identify whether the non-apical heart rate may be trusted as a true accurate measure of the patient's actual heart rate.

In the various embodiments of the invention, the apical heart rate 121, 131 is treated as a measure of the patient's true and accurate heart rate. In one or more embodiments, the HRVM 126, 136 may set the acceptable range of deviation as a number of heart beats away from the calculated apical heart rate. However, it should be appreciated that this range of deviation may be based on a parameter or factor other than heartbeat that is associated with the obtained heart rate.

After the non-apical heart rate is calculated, the HRVM 126, 136 compares the non-apical heart rate to the apical heart rate data to continue determining whether the patient is in need of medical attention, and outputs signals related thereto (e.g. the color coded heart rate displays). In doing so, the HRVM 126, 136 utilizes the calculated apical heart rate and the predefined acceptable range of deviation to calculate and generate an acceptable heart rate range. This heart rate range defines an acceptable apical heart rate range that the non-apical heart rate is allowed to fall within or deviate there-from.

For instance, if the calculated apical heart rate is measured at 100 BPM the predefined acceptable range of deviation may be set at being about 2 to about 5 heart beats away from the apical heart rate. As such, the acceptable heart rate range may be from 95 BPM to 105 BPM, and more preferably from 98 BPM to 102 BPM. In one or more embodiments, since the apical heart rate is continuously measured, the HRVM may take an average of multiple apical heart rate readings and use such average to determine the acceptable heart rate range (i.e., the 100 BPM in the above example may be an average calculated apical heart rate).

The HRVM 126, 136 then determines whether the calculated non-apical heart rate falls within the acceptable heart rate range, and if so, the process continues to step 260 (shown in FIGS. 7A and 7B). For instance, if the acceptable heart rate range has been calculated to range between 95 BPM to 105 BPM, and the non-apical heart rate is measured as being within such range (e.g., at 102 BPM), then the non-apical heart rate is recognized as a true, accurate reading of the patient's heart rate. In such an event, the non-apical heart rate reading is trusted by the medical personnel/team as a reliable reading of the patient's true heart rate. When the non-apical heart rate is trusted as an accurate heart rate measure, monitoring of the apical heart rate may be continued or stopped at any time. When the monitoring of the apical heart rate is stopped, apical heart rate monitoring may be restarted at a later time to verify that the non-apical heart rate continues to be a true, accurate measure of the patient's heart rate. In this exemplary embodiment, such a restart entails repeating steps 201, 210, 212, 214, 230 240, and 250.

In instances when the non-apical heart rate falls outside of the acceptable heart rate range, for example, if the measured and calculated non-apical heart rate of the invention falls outside the above exemplary range of 95 BPM to 105 BPM (e.g., the non-apical heart rate is 90 BPM, or 110 BPM, etc.) then the non-apical heart rate is not recognized as a reliable reading of the patient's true heart rate. When the non-apical heart rate falls outside of the acceptable heart rate range, both the apical heart rate and the non-apical heart rate continue to be monitored until a reading is obtained that ensures the medical team that the non-apical heart rate can be trusted as a reliable reading of the patient's true heart rate.

Referring to FIG. 7B, in those events when it has been determined that the non-apical heart is a reliable heart rate reading of the patient's true heart rate (i.e., that the non-apical heart falls within the acceptable heart rate range), then an alert is sent out to the medical personnel/team (step 260). This alert may be visual, auditory, or a combination of both visual and auditory. The alert indicates that the apical and non-apical heart rates are substantially the same, such that, the non-apical heart rate reading is reliable.

Again, from a start time of initiating apical heart rate monitoring, medical personnel are apprised (either visually or auditorily) of the patient's apical heart rate in an immediate and rapid response time, typically, within 3-10 seconds of initiating the apical heart rate reading. The apical heart rate is continuously monitored and refreshed from such time forward until it is determined that the calculated non-apical heart rate falls within the acceptable range of deviation from the apical heart rate. In such an event, the non-apical heart rate is considered to be a true accurate reflection of the patient's heart rate, and the apical heart rate monitoring may, or may not, be discontinued at this point.

Medical personnel may be alerted of such an event by an indicator on the display screen. For instance, while not meant to limit the invention, the alert may be output to the medical personnel/team via the unique indicator 127, 137. While this unique indicator 127, 137 may confirm receipt of the signal 112 from the actuator component 111, it may also be used to indicate reliable heart rate readings. The unique indicators 127, 137 may change appearance (e.g., stop flashing, flash more rapidly, change color, etc.) to indicate to the medical personnel that non-apical heart rate can be trusted as a true measure of the patient's actual heart rate.

Based on the apical and non-apical heart rate readings, the medical personnel/team may determine if the patient needs medical attention (step 262), and if so, provide patient with medical attention while continuing to monitor the patient in accordance with the invention. The patient may be continually monitored (step 264) until it is determined that the monitoring of the patient's heart rate and pulse may be stopped, at which point the first and second heart rate monitoring devices may be removed from the patient (step 266) and the process ended (step 300). It should be appreciated and understood that after the heart rate monitoring has stopped, monitoring of the patient's apical and non-apical heart rate may be restarted at a later time.

Referring to FIG. 7C, when it has been determined that the non-apical heart is not a reliable heart rate reading of the patient's true heart rate from step 250, then the HRVM determines whether the apical heart rate is less than the non-apical heart rate (or vice versa) (step 270). If the apical heart rate is less than the non-apical heart rate an error may exist. Both the devices of the invention are checked for error and the operator(s) may check for human errors (step 271). For instance, one of the devices of the invention may not be operating properly (e.g., battery level low, etc.), a device may not be applied properly to the patient such that reposition of the probe and/or pulse oximeter may be required, as well as replacement of the probe, pulse oximeter and/or operator(s). The process flow then repeats back to steps 201 and 202 for continued processing in accordance with the invention.

In step 270 if it is determined that the apical heart rate is not less than the non-apical heart rate, then the apical heart rate is greater than the non-apical heart rate. Again, since the apical heart rate is typically recognized as an accurate reflection of the patient's true heart rate, based on the apical heart rate, or the difference between the apical and non-apical heart rates, it may then be determined if the patient needs medical attention (step 272). For instance, while the apical may be greater than the non-apical heart rate, it may still be a low heart rate that requires immediate medical attention to the patient. The patient may then be provided with medical attention while continuing to monitor the patient's heart beat in accordance with the invention. The monitoring of the patient may be continued until it is determined that the monitoring of the patient's heart rate and pulse may be stopped (step 274), at which point the first and second heart rate monitoring devices may be removed from the patient (step 276) and the process ended (step 300).

In accordance with the various embodiments of the invention, it should be appreciated and understood that after the apical heart rate monitoring has stopped, monitoring of the apical heart rate may be restarted at a later time to verify that the non-apical heart rate continues to be a true, accurate reflection of the patient's heart rate. Also, depending on whether the apical heart rate is greater or less than the non-apical heart rate, both of which are output by the HRVM, the medical personnel are apprised of such measures via the outputs of the apical and non-apical heart rates, and may act upon such output rates accordingly. That is, the present invention simultaneously calculates both an apical heart rate and a non-apical heart rate, indicates a state of each either visually or auditorily, compares the non-apical heart rate to the apical heart rate to determine whether the non-apical heart rate is within acceptable tolerances of the apical heart rate (i.e., within the acceptable heart rate range), and displays all of these results to the medical personnel in a quick and efficient manner when time is of the essence.

In the various embodiments, both apical heart rate data and non-apical heart rate data are input into a single HRVM 126, 136. The HRVM 126, 136 calculates both the apical and non-apical heart rates, analyzes the two against one another, outputs a signal (either visual or auditory) to alert end-users of the current state of the patient's heart rate, and determines whether the non-apical heart rate may be trusted as a reliable reading of the patient's true heart rate, as well as verifies that the non-apical heart rate that has been determined as reliable remains reliable over time. The HRVM 126, 136 may have a single display (i.e., single monitor) that displays both the apical and non-apical heart rates as determined in accordance with the invention.

The systems and devices of the invention may be wirelessly operated devices, or portions thereof may include electrical wiring for the operation thereof. In one or more embodiments, the systems and devices of the invention are preferably of a size that is easily transported by medical personnel, and most preferably of a size that may fit into the medical personnel's pocket. The systems and devices are preferably easy to use, efficient, low-cost, require low power usage, and operate over multiple wireless channels. Each of the systems and devices of the invention may be provided with protective covers for infection control and repeated use of such systems and devices. Alternatively, one or more of the system components and devices may be single use, disposable items. The systems and devices are also preferably constructed of materials that allow for such systems and devices to be cleaned by any known cleaning and/or sanitizing methods and means.

The methods, systems and devices of the various embodiments of the invention provide fast, accurate, reliable and verified heart rate measures, and do so in high intensity environments that have minimal time (e.g., a few seconds) in which to take action and provide the patient with required medical attention. The invention also prevents unnecessary interventions during resuscitation.

While not meant to be limiting in any way, the first heart rate monitoring device 100 may be any type of device that measures or detects apical heart rate. For instance, in one or more embodiments the first heart rate monitoring device 100 may be a stethoscope, such as that disclosed in PCT Patent Application No. PCT/US2011/036029, which is incorporated below. FIGS. 8-12D show one or more embodiments of components and devices suitable for use in obtaining the apical heart rates 121, 131 in accordance with the invention. The following description and related drawings are for illustration purposes only to detail an exemplary embodiment of the invention, and by no means are meant to limit or restrict the various embodiments of the present invention. It should be appreciated and understood that these components are used in conjunction with at least the second heart rate monitoring device 120 and the HRVM 126, 136 of the invention.

Figure 8:
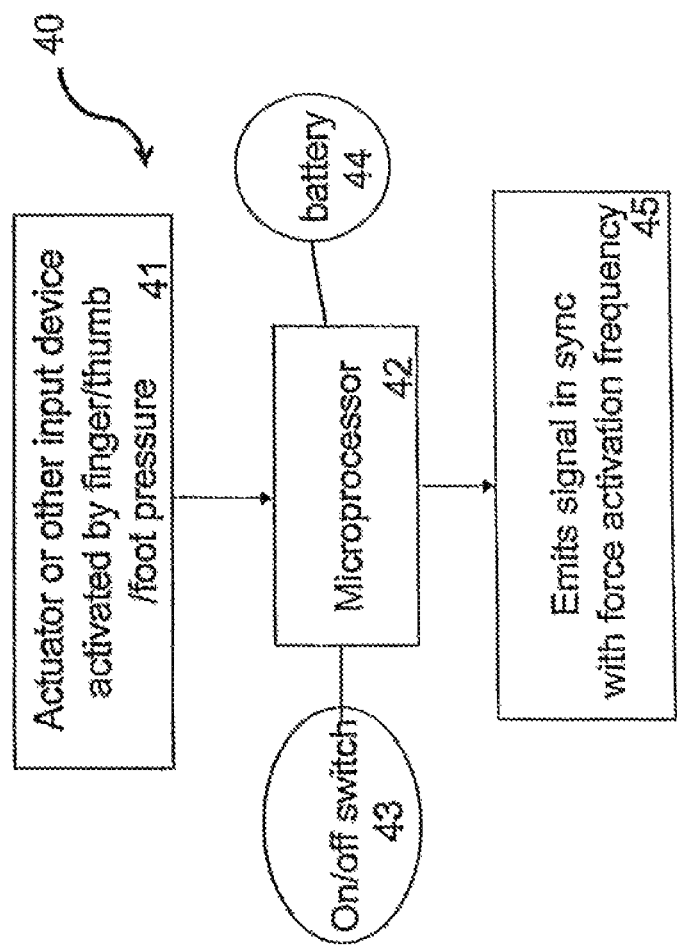
FIG. 8 illustrates a first heart rate monitoring device suitable for use in the invention.

Referring to FIG. 8 an actuator 41 (or other input device such as a mechanical, electrical, magnetic, infrared, microwave or other device that detects motion) is positioned such that a user that is auscultating the patient can input a heartbeat event every time such person hears a heartbeat by triggering the actuator 41 with a thumb, finger, foot or other manual input. The actuator 41 is connected to a microprocessor 42 that is in communication with an off/switch 43 and/or a battery 44 that powers the microprocessor 42. The microprocessor 42 receives the output from the actuator 41. It has a set of instructions therein for determining the heartbeats per minute based on the time that has elapsed. In so doing, the microprocessor 42 uses the data input from the actuator 41 and calculates a time interval between inputs by comparing to a timer or clock with as few as two output signals from the actuator to determine the number of heartbeats per minute. The microprocessor 42 then sends a output signal that indicates visually and/or aurally each heartbeat, the number of heartbeats per minute, an indicator of the time that has elapsed (e.g., every 30 seconds), a graph that tracks the on-going measurement of the heart rate, and a display that changes color, shape, vector or other indication of the heart rate of the patient.

Figure 9:
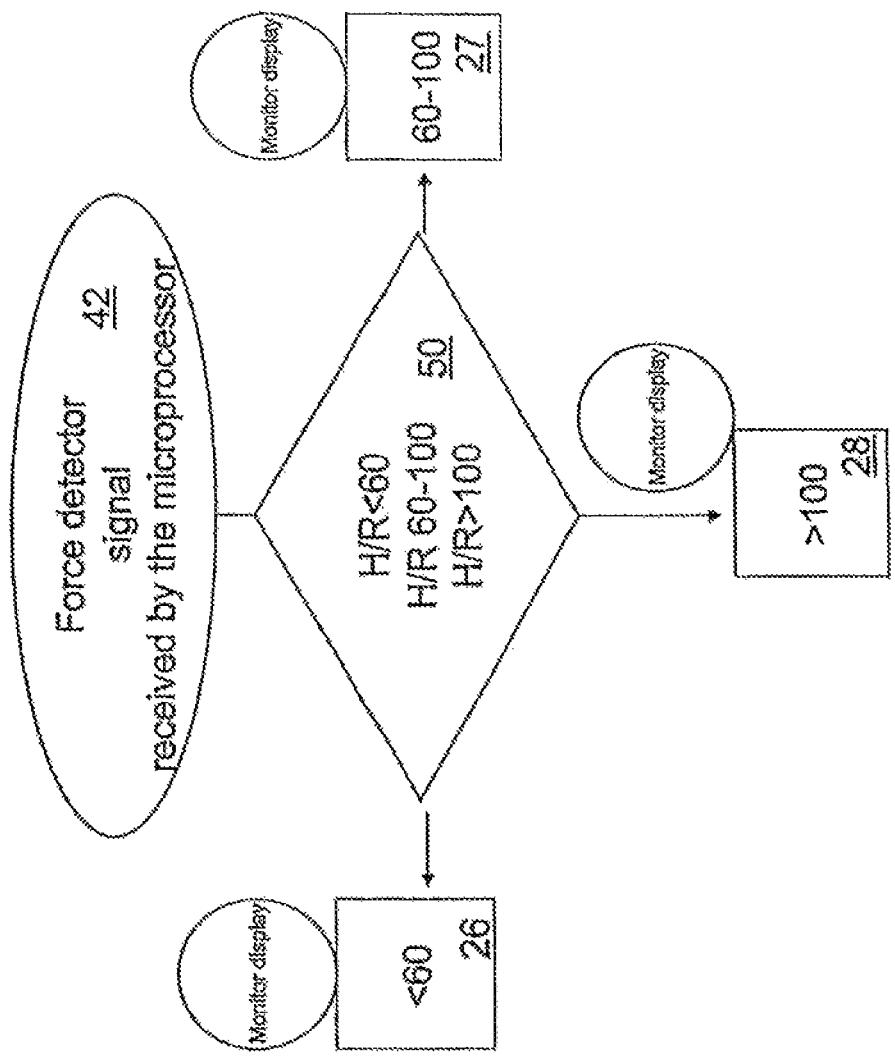
FIG. 9 illustrates a flowchart of data processing and processor output.

FIG. 9 shows a flowchart of the data processing and processor output suitable for use in one or more embodiments of the invention using, for instance, a device 40 as shown in FIG. 8. The microprocessor 42 calculates the heart rate 50 using the data input from the actuator 41, and outputs such calculated heart rate at the display monitor. The display monitor shows the output heart rate data using unique indicator(s) or identifier(s), such as, the actual numerical heart rate, a color indicator (e.g., red, yellow/orange and green), or a combination of the two in outputs, thereby notifying all medical personnel attending to the infant whether such infant has a heart rate of less than 60 per minute (26), between 60 and 100 per minute (27), or greater than 100 (28) heartbeats per minute.

Figure 10:
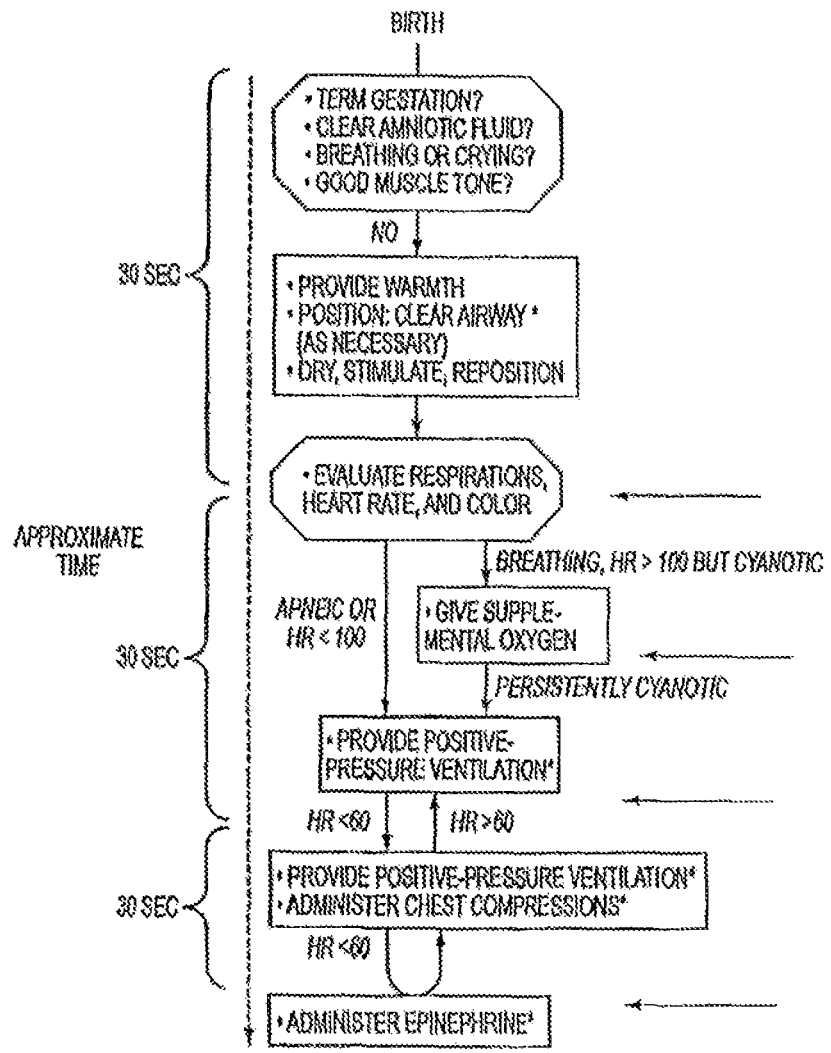
FIG. 10 illustrates a NRP/AAP Resuscitation Flow Chart demonstrating timelines involved in decision-making showing times at which use and/or implementation of the invention are beneficial.

FIG. 10 is a standard NRP/AAP Resuscitation Flow Chart that demonstrates the timelines involved in decision-making and represents the times during which various devices, systems and methods of the present invention are critical. The different arrows show the times at which the invention may be implemented to allow the medical team to make determinations that heretofore were based on mental calculations, and for which, the present invention allows for the first time to meet the need of the medical team to provide accurate data on the heart rate of the infant.

Figure 11A:
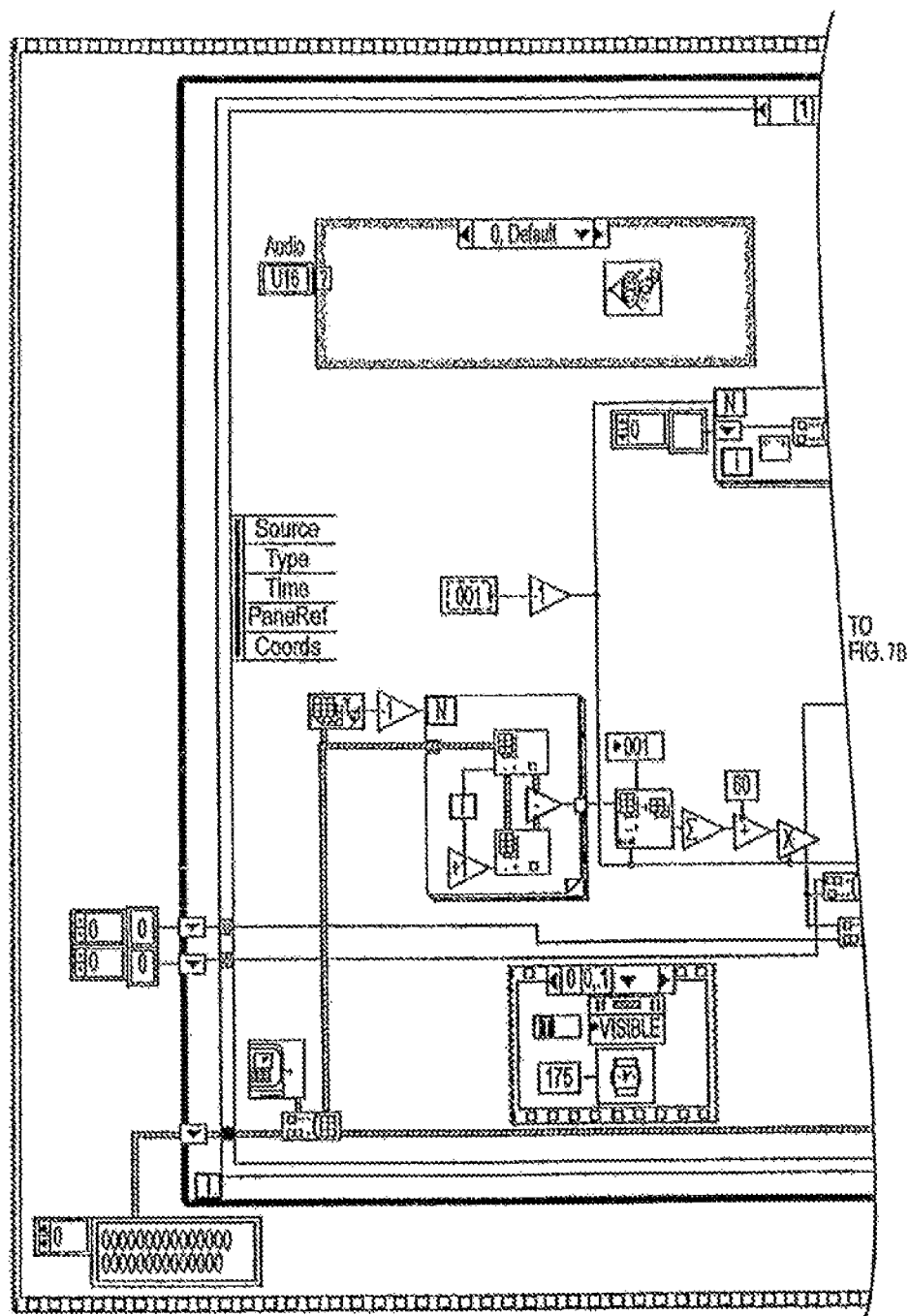
FIGS. 11A-C sequentially illustrate a flowchart of one or more processor implementations that may be used as part of the data processing of various embodiments of the invention.
Figure 11B:
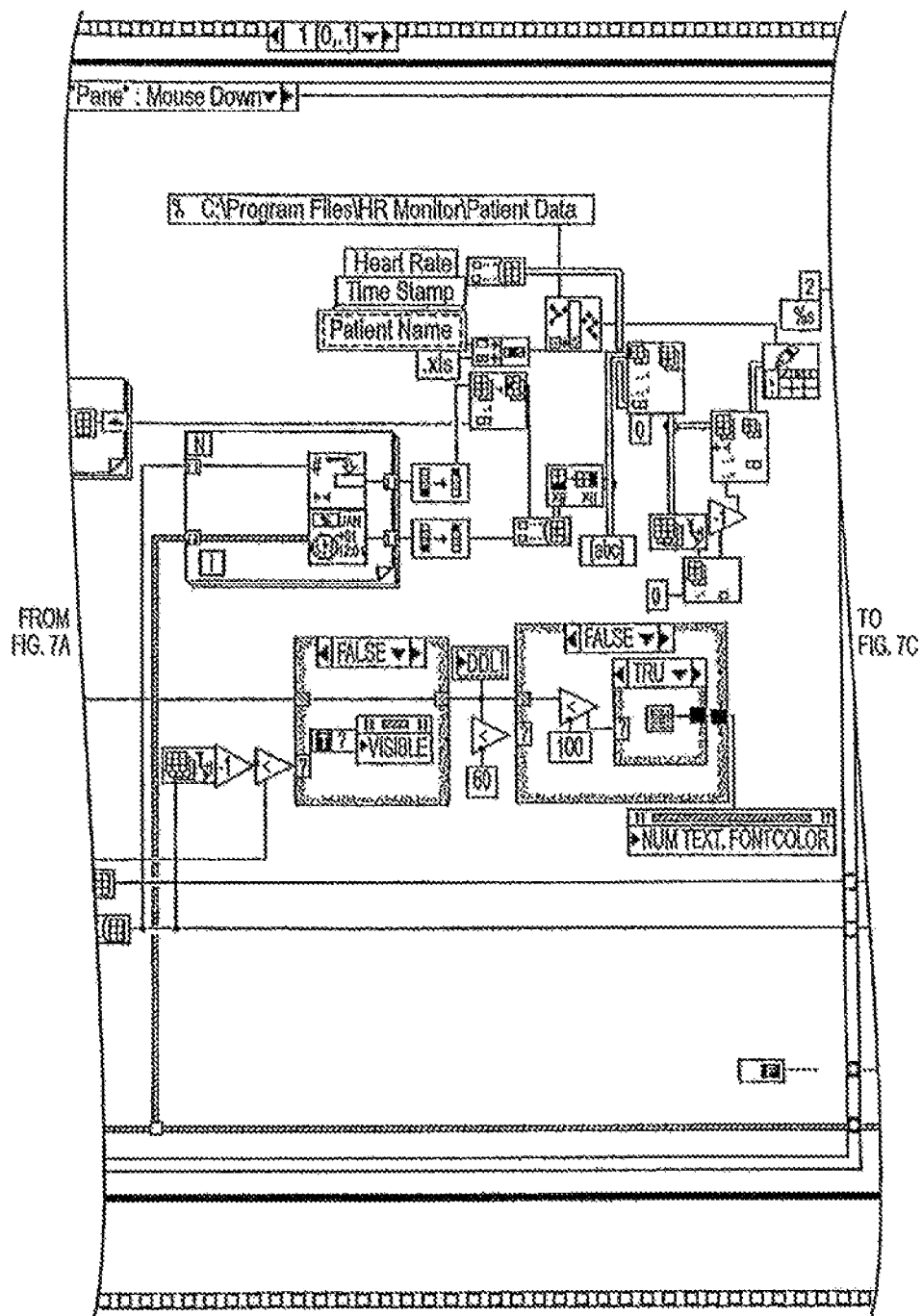
Figure 11C:
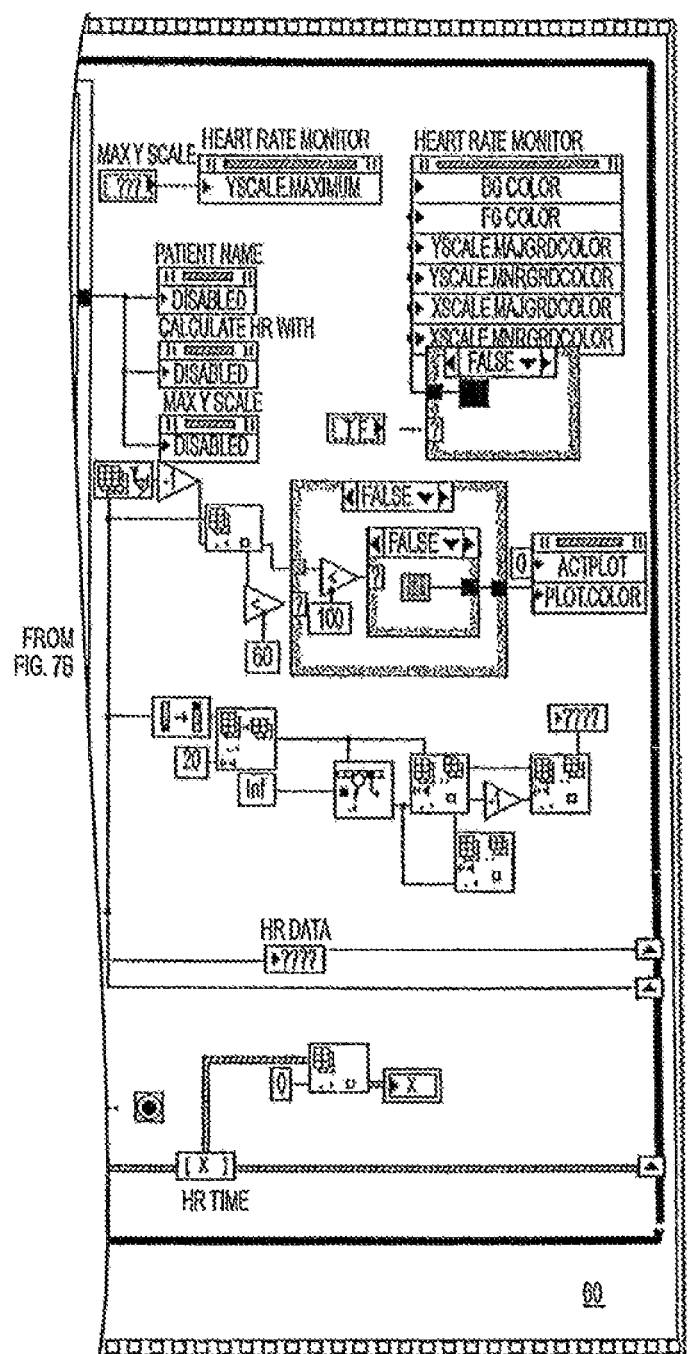

FIGS. 11A-C illustrate an example of a flowchart of one or more processor implementations that may be used as part of the data processing. The Heart Rate Monitor program was designed using LabView, which is a graphical programming environment. LabView is a coding product of National Instruments (Austin, Tex.). The skilled artisan will recognize that other coding environments and/or computer languages may be used to provide the functionality of the various embodiments of the invention.

One or more embodiments of the invention may include a set of instructions (e.g., a program) contained in a stacked sequence structure consisting of two, or more, frames. The first frame initializes the graph and the numeric display arrays with no data. This frame also loads the picture (.jpg) of the heart. The second frame (64) of the stacked sequence structure contains a while loop. A while loop repeats a subdiagram inside it until forced to stop either by a conditional terminal, in this case by selecting the "Write Log" button, or by manually aborting the program by selecting a stop sign. The while loop has three (3) shift registers; one for the heart rate numerical display, one for the graphical display, and one for the time stamp that is created with each actuator click. In the while loop there is an event structure, which has one or more subdiagrams, or event cases, exactly one of which executes when the structure executes. The event structure waits until an event happens then executes the appropriate case to handle that event. There are three frames in the event structure, frame 0, 1, and 2. Event 0 is the timeout frame. No code is present here. An actuator click, or more specifically the actuator down position, activates frame 1 of the event structure. After the actuator click, which activates the code in frame 1, the event structure advances to frame. If the "Write Log" button is pressed the program ends and an Excel (.xls) file may be written with the patient's name (default value: John Doe) with an ".xls" extension and be placed in a directory (e.g., directory—C:\Program Files\HR Monitor\Patient Data). If the "Write Log" button is not pressed, the shift registers may be used to carry over the values from the last iteration to the next iteration, thereby building up the arrays of data for the time stamps added from the actuator down position and the heart rate calculated from these time stamp intervals.

In these embodiments, it is in the event structure in frame 1 when the actuator is in the down position where the heart rate calculation is generated and displayed. An array consisting of a time stamp is created and initialized. Each actuator click adds that time stamp to the array. The interval between each actuator click is calculated. The user selects the number of heartbeats to use for the heart rate calculation. The default value is three. This number is then decremented by 1. This is the number of most recent intervals that is summed together, then divided into 60 seconds, and then multiplied by that decremented number to give the heart rate. The number of heartbeats selected may not be calculated correctly until that number is reached and therefore the numeric and graphical display may not be visible until such number is reached. These numbers may not be present in the .xls file.

In this event structure frame, the audio files are loaded. The selected audio activates with each actuator click as well as the .jpg file. The last heart rate value is taken and the color of the numeric and graphical heart rate is selected (e.g., red if the heart rate is under 60 heartbeats per minute, orange if between 60 and 99 heartbeats per minute, and green if 100 or above heartbeats per minute).

The following is an example of one or more embodiments of a set of instructions for implementing the invention. These instructions may be initiated by double clicking on a Heart Rate Monitor executable file (Heart Rate Monitor.exe). In this example, the program begins as the "Elapsed Time (s)" box begins to increment in seconds. This value is not used for calculation purposes. The Tab key allows the user to navigate from control to control. Tab order may be set to:

1. Patient Name—input patient name that may be used to name a data log file (.xls). Default value is John Doe.

2. Audio—a drop down menu with options for a computer beep, silent, or 2 options for .wav files. Default value is Heart Monitor 1.wav 3. Calculate HR with # of heartbeats—The number selected in this box may use the time between that number of last actuator clicks to calculate the current heart rate. The time between the last number of actuator clicks are added up, then divided by 60, and finally multiplied by the number selected minus one to result in current heart rate. When the program begins, a numeric heart rate may not be shown until that number of actuator clicks selected has been reached in order to maintain accuracy. If at any time during the program execution the program remains idle, the heartbeat accuracy may not be achieved until that selected number of actuator clicks is achieved again. Recommended and default value here is 3.

4. Select the maximum value for the Y-scale—This allows the user to change the y-scale maximum value on the graph, which represents heartbeats per minute. The default value is set at 200.

5. Write to log file—Upon completion of use, selecting this button uses the name in the Patient Name box to create a Microsoft Excel (Name.xls) file located in C:\Program Files\HR Monitor\Patient Data. The table below is an example.

| Heart Rate | Time Stamp |
|---|---|
|  | 3/24/2010 14:35 |
|  | 3/24/2010 14:35 |
|  | 3/24/2010 14:35 |
| 55 | 3/24/2010 14:35 |
| 55 | 3/24/2010 14:35 |
| 56 | 3/24/2010 14:35 |
| 51 | 3/24/2010 14:35 |
| 53 | 3/24/2010 14:35 |
| 57 | 3/24/2010 14:35 |
| 70 | 3/24/2010 14:35 |
| 83 | 3/24/2010 14:35 |
| 92 | 3/24/2010 14:35 |
| 101 | 3/24/2010 14:35 |
| 91 | 3/24/2010 14:35 |
| 80 | 3/24/2010 14:35 |
| 76 | 3/24/2010 14:35 |
| 80 | 3/24/2010 14:35 |

In the invention it is possible in Excel to further expand the Time Stamp to include seconds, if desired, through the Format→Cells→Number→Custom menu. Under Type, select "m/d/yyyy h:mm" option and manually append ":ss". Then select OK. Selecting the Write Log button may not allow any further data collection. The program may have to be stopped and run again. It is possible in Excel to further expand the Time Stamp to include seconds, if desired, through the Format→Cells→Number→Custom menu. Under Type, select "m/d/yyyy h:mm" option and manually append ":ss". Then select OK. Selecting the Write Log button may not allow any further data collection. The program may have to be stopped and run again.

Selecting the Tab key again brings the User back to Patient Name. In order to input a patient's name, press the Tab key once after the program is running. The program should be started after opening the executable file although it may be stopped at any time by pressing a RED Stop Sign located in the top left of the window. Selecting the Arrow to it's left can restart the program. Upon completion of entering the patient's name, select the Tab key again, and then select the preferred Audio setting. Select the Tab key again, and then select the number of consecutive heartbeats desired to calculate current heart rate. If any of the default values are satisfactory, the Tab key may continue to be used to circulate through the options.

Heart rate calculation will begin as soon as an actuator click is initiated INSIDE the program window. The Patient Name box and Calculate HR with # of heartbeats may be grayed out and not reset until termination of the program. It is preferred that the actuator clicks coincide with the heartbeats as closely as possible for accuracy. The current rate may be shown numerically in the top left corner of the program window. A picture of a heart (.jpg) acts as a visual aid, and appears with each click of the actuator, as well as the audio preference (if silent mode is not selected). The displayed heart rate is color-coded based upon the current heart rate as well as the graph on the lower half of the program window.

For instance, the color codes may be:
Heart Rate under 60 heartbeats per minute=RED
Heart Rate between 60-100 heartbeats per minute=ORANGE/YELLOW
Heart Rate 100 heartbeats per minute and over=GREEN The graph, which may be located on a bottom half of the program window, may hold the last registered heartbeats, e.g., a maximum of the last 20 heartbeats. The most current heart rate reading appears along the y-scale located on the right side of the graph, which reads in chronological order from left to right. Data is stored, and as such, is not lost if such data is not displayed on the graph. Preferable, all heartbeat data is stored in memory and is written to a data log file.

FIGS. 12A-D illustrate examples screen shots of Heart Rate Monitors displaying outputs. These outputs display various numerical heart rates 70, including, but not limited to a display of 68 heartbeats per minute (FIG. 8), a display of 52 heartbeats per minute (FIG. 9), and a display of 142 heartbeats per minute (FIG. 10). Again, these displayed heartbeats may be color coded, e.g., the 68 of FIG. 8 may be displayed in orange, the 52 of FIG. 9 may be displayed in red, and the 142 of FIG. 10 may be displayed in green.

Figure 12A:
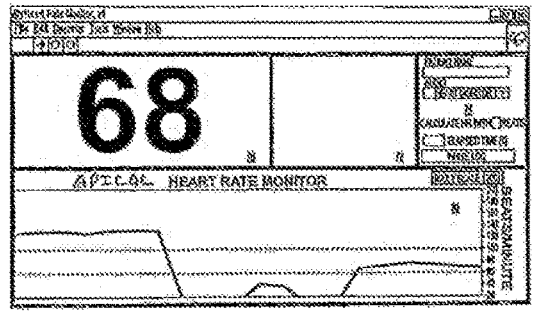
FIGS. 12A-D illustrate outputs of data generated from devices suitable for use with the invention.
Figure 12B:
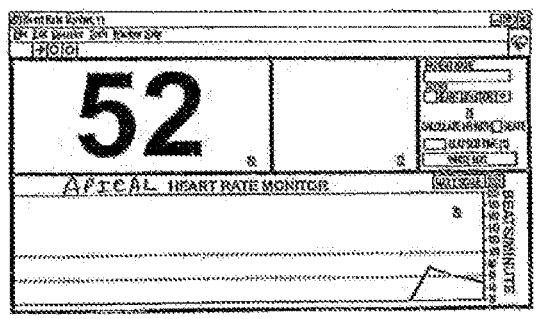
Figure 12C:
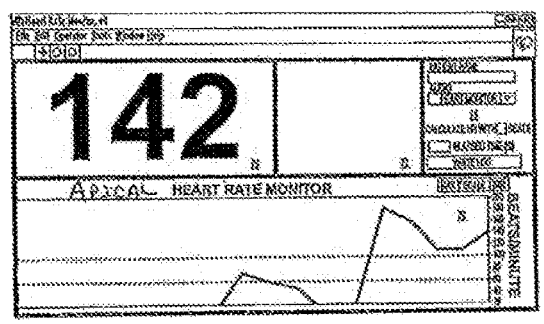
Figure 12D:
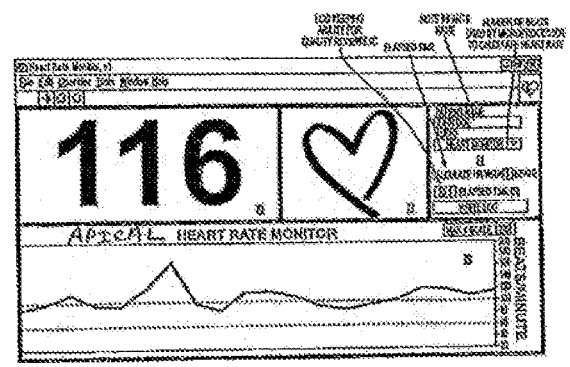

FIG. 12D shows that each time a user inputs a heartbeat, a heart 72, or like indicator, is depicted adjacent the numerical heart rate indicator. Below the heart rate 70, is a graph 74 that shows the measured number of heartbeats in real-time. This graph may also change color as the heart rate changes over time. Patient, and optionally user information, is depicted to the right of the heart 72 in box 76. FIG. 11 also shows further details of screen displays, including, but not limited to, displaying the time elapsed, a variable input parameter that is used to calculate the number of heartbeats used to calculate the heart rate (in this case, depicted as three heartbeats per calculation), whether an audio output is provided, patient information, and whether to write a log of the calculations.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

Furthermore, aspects of the present invention may take the form of a computer program product embodied in one or more computer readable medium(s) having computer readable program code embodied thereon. Any combination of one or more computer readable medium(s) may be utilized. The computer readable medium may be a computer readable signal medium or a computer readable storage medium.

A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in base band or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the end-user's computing device (such as, a computer), partly on the end-user's computing device, as a stand-alone software package, partly on the end-user's computing device and partly on a remote computing device or entirely on the remote computing device or server. In the latter scenario, the remote computing device may be connected to the end-user's computing device through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions.

The computer program instructions may be provided to a processor of a general purpose computing device (such as, a computerized device), special purpose computing device, or other programmable data processing apparatus to produce a machine, such that the instructions, which execute via the processor of the computing device or other programmable data processing apparatus, create means for implementing the functions/acts specified in the flowchart and/or block diagram block or blocks.

The computer program instructions may also be stored in a computer readable medium that can direct a computing device, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computing device (such as, a computer), other programmable apparatus or other devices to produce a computer implemented process such that the instructions which execute on the computer or other programmable apparatus provide processes for implementing the functions/acts specified in the flowchart and/or block diagram block or blocks.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or."

The term "or combinations thereof" as used herein refers to all permutations and combinations of the listed items preceding the term. For example, "A, B, C, or combinations thereof" is intended to include at least one of: A, B, C, AB, AC, BC, or ABC, in any order as well as repeats of one or more item, such as BB, AAA, BBC, etc.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A method of obtaining heart rate of a newborn immediately after birth comprising:
   providing a wireless pulse oximeter having a size that allows attachment to a newborn;
   securing the wireless pulse oximeter to the newborn immediately after birth;
   obtaining non-apical heart rate data of the newborn using a first heart rate monitoring device comprising the wireless pulse oximeter;
   transmitting the non-apical heart rate data via a first signal to a processor performing heart rate verification;
   calculating a non-apical heart rate measure using the processor;

outputting to a display an identification that identifies the non-apical heart rate measure of the newborn immediately after birth;
obtaining apical heart rate data using a second heart rate monitoring device comprising a stethoscope;
transmitting the apical heart rate data to the processor;
calculating an apical heart rate measure using in the processor;
generating an acceptable heart rate range using the apical heart rate measure using in the processor;
determining whether the non-apical heart rate measure falls within or outside the acceptable heart rate range; and
outputting to the display an identification that identifies the non-apical heart rate measure as falling within or outside the acceptable heart rate range, and when the non-apical heart rate measure falls within the acceptable heart rate range it is identified as a reliable measure of a true heart rate; and
when the reliable measure of the true heart rate is detected,
outputting the identification within the first few seconds to minutes after birth of the newborn and alerts medical personnel whether the newborn needs active resuscitation, close observation, or is vigorous and needs no resuscitation.

2. The method of claim 1, wherein the apical heart rate is obtained using the stethoscope in combination with an actuator component that outputs a second signal corresponding to the apical heart rate data to the heart rate verification module.

3. The method of claim 2, wherein the actuator component is attached to the stethoscope.

4. The method of claim 2, wherein the actuator component is separate and distinct from the stethoscope.

5. The method of claim 2, wherein the second signal comprises a wireless signal.

6. The method of claim 1, wherein the processor resides within the stethoscope.

7. The method of claim 2, wherein the pulse oximeter wirelessly transmits the signal to the processor within the stethoscope.

8. The method of claim 1, wherein the processor resides within the pulse oximeter.

9. The method of claim 1, wherein the processor resides within a component separate from the first and second heart rate monitoring devices.

10. The method of claim 1 further including outputting both the calculated apical and non-apical heart rate measures to an end-user within about 3-10 seconds from obtaining the apical heart rate data.

11. The method of claim 1, wherein if the non-apical heart rate measure falls within the acceptable heart rate range, then the non-apical heart rate measure is recognized as said reliable measure of said true heart rate.

12. The method of claim 11 further including ceasing obtaining the apical heart rate data when the non-apical heart rate measure falls within the acceptable heart rate range.

13. The method of claim 12 further including validating that the non-apical heart rate remains to fall within the acceptable heart rate range such that it continues to be the reliable measure of the true heart rate.

14. The method of claim 1, wherein if the non-apical heart rate measure is outside the acceptable heart rate range, then the non-apical heart rate measure is unreliable, and both the apical and non-apical heart rate measures are continued to be monitored and output.

15. The method of claim 1, wherein the apical heart rate data is manually obtained while the non-apical heart rate data is electronically obtained.

16. The method of claim 1 further including the display having a unique identifier that alerts the medical personnel that the newborn needs said active resuscitation or said close observation within said first few seconds to minutes after birth.

17. The method of claim 1, wherein both the apical heart rate data and the non-apical heart rate data are continuously obtained.

18. The method of claim 1 further including outputting the calculated apical and non-apical heart rate measures to one or more medical personnel, the one or more medical personnel making a determination based on the output apical and non-apical heart rate measures as to any required medical attention and immediately administering any said required medical attention within said first few seconds to minutes after birth.

19. A system for obtaining heart rate of a newborn immediately after birth comprising:
a wireless pulse oximeter configured to be secured to the newborn immediately after birth and to generate non-apical heart rate data;
a stethoscope configured to obtain apical heart rate data from the newborn, the stethoscope being further configured to transmit the apical heart rate data;
a display;
a processor configured to
receive the non-apical heart rate data and the apical heart rate data;
calculate a non-apical heart rate measure from the non-apical heart rate data;
calculate an apical heart rate measure from the apical heart rate data;
immediately output to the display the non-apical heart rate measure; and
generate an acceptable heart rate range based on the apical heart rate measure; and
wherein, the processor is further configured to output an identification output by the display that identifies the non-apical measure as falling within or outside the acceptable heart rate range to verify whether the non-apical heart rate measure is a reliable measure of a true heart rate of the newborn, wherein the identification output occurs within the first few seconds to minutes after the birth of the newborn and alerts medical personnel that the newborn needs active resuscitation, close observation, or is vigorous and needs no resuscitation.

20. The system of claim 19 wherein the processor is integral with the wireless pulse oximeter, the stethoscope, or an electronic device separate from the wireless pulse oximeter and the stethoscope.

* * * * *

UNITED STATES PATENT AND TRADEMARK OFFICE
CERTIFICATE OF CORRECTION

PATENT NO.         : 9,883,837 B2
APPLICATION NO.    : 14/348258
DATED              : February 6, 2018
INVENTOR(S)        : Johnathan M. Whitfield Page 1 of 1

It is certified that error appears in the above-identified patent and that said Letters Patent is hereby corrected as shown below:

In the Specification

In Column 16, Line 30, delete "frame" and substitute therefore -- frame 2 --

Signed and Sealed this
Twenty-eighth Day of August, 2018

Andrei Iancu
*Director of the United States Patent and Trademark Office*